US011707444B2

United States Patent
Lee et al.

(10) Patent No.: US 11,707,444 B2
(45) Date of Patent: Jul. 25, 2023

(54) ANTIVIRAL COMPOSITION FOR SARS-COV-2 CONTAINING CANNABINOIDS AS ACTIVE INGREDIENT

(71) Applicants: RESEARCH COOPERATION FOUNDATION OF YEUNGNAM UNIVERSITY, Gyeongsan-si (KR); KOREA INSTITUTE OF SCIENCE AND TECHNOLOGY, Seoul (KR)

(72) Inventors: Jintae Lee, Daegu (KR); Jungyeob Ham, Gangneung-si (KR); Taejung Kim, Gangneung-si (KR)

(73) Assignees: RESEARCH COOPERATION FOUNDATION OF YEUNGNAM UNIVERSITY, Gyeongsan-si (KR); KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 12 days.

(21) Appl. No.: 17/465,847

(22) Filed: Sep. 3, 2021

(65) Prior Publication Data

US 2022/0096425 A1    Mar. 31, 2022

(30) Foreign Application Priority Data

Sep. 29, 2020    (KR) .................. 10-2020-0126496

(51) Int. Cl.

| | |
|---|---|
| *A61K 31/352* | (2006.01) |
| *A61K 31/192* | (2006.01) |
| *A61K 31/05* | (2006.01) |
| *A61K 31/513* | (2006.01) |
| *A61K 31/4706* | (2006.01) |
| *A61P 31/14* | (2006.01) |
| *A61K 36/185* | (2006.01) |
| *G01N 33/94* | (2006.01) |
| *G01N 33/569* | (2006.01) |
| *A61K 31/675* | (2006.01) |

(52) U.S. Cl.
CPC ............ *A61K 31/352* (2013.01); *A61K 31/05* (2013.01); *A61K 31/192* (2013.01); *A61K 31/4706* (2013.01); *A61K 31/513* (2013.01); *A61K 31/675* (2013.01); *A61K 36/185* (2013.01); *A61P 31/14* (2018.01); *G01N 33/56983* (2013.01); *G01N 33/948* (2013.01); *G01N 2333/165* (2013.01); *G01N 2500/04* (2013.01)

(58) Field of Classification Search
CPC .................................................. A61K 31/352
See application file for complete search history.

(56) References Cited

U.S. PATENT DOCUMENTS 11,154,531 B2 * 10/2021 Tsai ................... A61K 39/3955

FOREIGN PATENT DOCUMENTS

CN    111686095 A    9/2020

OTHER PUBLICATIONS

Costiniuk, Cytokine Growth Factor Rev. 53, 63-65 (2020).*
Rossi F, Int. J. Mol. Sci. 21(11), E3809. doi:10.3390/ijms21113809 (2020).*
Manli Wang et al, "Remdesivir and chloroquine effectively inhibit the recently emerged novel coronavirus (2019-nCoV) in vitro", Cell Research (2020) 30:269-271; https://doi.org/10.1038/s41422-020-0282-0.
Emmanuel Shan Onaivi et al, "Cannabis for COVID-19: can cannabinoids quell the cytokine storm?", Future Sci OA. Sep. 2020; 6(8): FSO625.
Abd Al-Aziz A. Abu-Saleh et al, "Discovery of potent inhibitors for SARS-CoV-2's main protease by ligand-based/structure-based virtual screening, MD simulations, and binding energy calculations", Physical Chemistry Chemical Physics, 2020, 22, pp. 23099-23106.
Fasinu, P.S. et al, "Current status and prospects for cannabidiol preparations as new therapeutic agents", Pharmacotherapy, vol. 36, No. 7, 2016, pp. 781-796.
Gurung, A.B. et al, "Unravelling lead antiviral phytochemicals for the inhibition of SARS-CoV-2 MPro enzyme through in silico approach", Life Sciences, vol. 255, Aug. 15, 2020, 255:117831.
Valerie Vaillancourt et al, "A One-Step Method for the α-Arylation of Camphor. Synthesis of (−)-Cannabidiol and (−)-Cannabidiol Dimethyl Ether", J. Org. Chem. 1992, 57, 3627-3631.
Daniel Seeliger et al., "Ligand docking and binding site analysis with PyMOL and Autodock/Vina", J Comput Aided Mol Des (2010) 24:417-422.
Oleg Trott et al, "Software News and Update AutoDock Vina: Improving the Speed and Accuracy of Docking with a New Scoring Function, Efficient Optimization, and Multithreading", Journal of Computational Chemistry, vol. 31, No. 2, 2009, pp. 455-461.
Elmar Krieger et al, "YASARA View—molecular graphics for all devices—from smartphones to workstations", Bioinformatics, Oct. 15, 2014, vol. 30 No. 20 2014, pp. 2981-2982.
Sangeun Jeon et al, "Identification of Antiviral Drug Candidates against SARS-CoV-2 from FDA-Approved Drugs", Antimicrobial Agents and Chemotherapy, Jul. 2020, vol. 64, Issue 7, e00819-20.
Cecilia T Costiniuk et al, "Oral cannabinoids in people living with HIV on effective antiretroviral therapy: CTN PT028—study protocol for a pilot randomised trial to assess safety, tolerability and effect on immune activation", BMJ Open, Jan. 17, 2019;9(1):e024793. doi: 10.1136/bmjopen-2018-024793.
Timna Naftali et al, "Low-Dose Cannabidiol Is Safe but Not Effective in the Treatment for Crohn's Disease, a Randomized Controlled Trial", Dig Dis Sci (2017) 62:1615-1620.

* cited by examiner

*Primary Examiner* — Nizal S Chandrakumar
(74) *Attorney, Agent, or Firm* — Revolution IP, PLLC

(57) ABSTRACT

The present invention relates to an antiviral composition and a screening method thereof for severe acute respiratory syndrome coronavirus 2 (SARS-CoV-2) that occurred in Wuhan, China in 2019. An extract from leaves or unfertilized female flowers of *Cannabis sativa* L. or its fraction, and the cannabinoids (CBDs) molecules isolated from it have high binding strength and stability to SARS-CoV-2 MP$^{pro}$, thereby inhibiting its action as the main protease, to provide a useful lead molecule that can be used alone or in combination with other drugs to treat SARS-CoV-2.

9 Claims, 26 Drawing Sheets

ABSTRACT# ANTIVIRAL COMPOSITION FOR SARS-COV-2 CONTAINING CANNABINOIDS AS ACTIVE INGREDIENT

CROSS-REFERENCE TO RELATED APPLICATION

This application claims priority to and the benefit of Korean Patent Application No. 10-2020-0126496 filed in the Korean Intellectual Property Office on Sep. 29, 2020, the entire contents of which are incorporated herein by reference.

BACKGROUND OF THE DISCLOSURE

1. Field of the Disclosure

The present invention relates to an antiviral composition and a screening method thereof for severe acute respiratory syndrome coronavirus 2 (SARS-CoV-2) that occurred in Wuhan, China in 2019, and an extract from leaves or unfertilized female flowers of Cannabis sativa L. or its fraction; and the cannabinoids (CBDs) molecules isolated therefrom have high binding strength and stability to SARS-CoV-2 $M^{Pro}$, thereby inhibiting its action as the main protease, to provide a useful lead molecule that can be used alone or in combination with other drugs to treat SARS-CoV-2.

2. Description of the Related Art

Corona virus disease 19 (COVID-19) is a respiratory infectious disease that first occurred in Wuhan, China in December 2019 and has spread worldwide. Its pathogen was identified on Jan. 9, 2020, when the World Health Organization (WHO) revealed that the cause of the pneumonia was a new type of severe acute respiratory syndrome coronavirus 2 (SARS-CoV-2, named by the International Classification of Viruses on February 11).

Severe acute respiratory syndrome coronavirus 2 (SARS-CoV-2) shares 79% genetic similarity with SARS coronavirus (SARS-CoV), and interestingly, the known coronavirus sequence shares more than 98% similarity to bat coronavirus RaTG13. Alpha (α), beta (β), gamma (γ), and delta (δ) are used to denote subcategories of the coronavirus family.

SARS-CoV-2, MERS-CoV, and SARS-CoV infect only the lower respiratory tract to cause pneumonia, whereas human coronavirusep 229E, NL63, OC43, and HKU1 are usually related to mild symptoms associated with infection of the upper respiratory tract.

The SARS-CoV-2 genome encodes about 25 proteins required for viruses to infect and replicate in humans, one of which, the spike (S) protein, recognizes and binds to Angiotensin-converting enzyme 2 to start virus infection. Two proteases cleave viral and human proteins, and RNA polymerase synthesizes viral RNA and viral RNA-cleaving endoribonuclease. In particular, 'SARS-CoV-2 $M^{Pro}$' or '$M^{Pro}$', called the viral Main Protease, is considered the best molecular target to block the replication of the coronavirus. It is an enzyme which properly cuts produced proteins to causes the SARS-CoV-2 virus to multiply in cells.

More specifically, the SARS-CoV-2 main protease $M^{Pro}$ (also called $3CL^{Pro}$) is known to play a major role in the viral life cycle. SARS-CoV-2 $M^{Pro}$ protease and papain-like protease processes translate viral RNA polyprotein, and SARS-CoV-2 $M^{Pro}$ recognizes and acts on less than 11 cleavage sites of Leu-Gln↓ (Ser, Ala, Gly) of the polyprotein replicase 1ab.

Accordingly, there is a need to discover a group of drug candidates which can effectively bind to the SARS-CoV-2 $M^{Pro}$ protease and interfere with its action. In addition, inhibition of the SARS-CoV-2 $M^{Pro}$ protease is unlikely to be toxic to humans as similar cleavage specificities have not been reported for human proteases.

Severe acute respiratory syndrome coronavirus 2 (SARS-CoV-2) is known to be transmitted when droplets (saliva) of an infected person penetrate the respiratory tract or the mucous membrane of the eyes, nose, or mouth. After the incubation period of about 2 to 14 days (estimation) after infection, fever (37.5° C.), respiratory symptoms such as cough or difficulty breathing, and pneumonia appear as the main symptoms, but rare cases of asymptomatic infection also have been reported.

More specifically, recently, it has been reported that inflammatory molecules (e.g., C reactive protein and pro-inflammatory cytokines, IL-1β, IL-6, IL-7, IL-8, IL-9, IL-10, fibroblast growth factor, IFN, granulocyte-colony-stimulating factor, granulocyte-macrophage colony-stimulating factor, macrophage inflammatory protein 1 α, tumor necrosis factor and vascular endothelial growth factor) are elevated in lung cells of SARS-CoV-2 infected patients. In this study, the presence of these proinflammatory cytokines in the lung has been reported to be associated with acute respiratory distress, serious injury, and death.

Viral replication is associated with inflammation and immune activation of the host, and it has been demonstrated that cannabinoid receptor type 2 (CB-2) is expressed at high levels in immune cells (e.g., B cells, natural killer cells, CD8 lymphocytes, monocytes, CD4 lymphocytes and neutrophils) in the lungs, liver, nasal epithelium, spleen, thymus, kidney, and brain.

Cannabinoid's receptor-2 (CB-2) is best known for its immunosuppressive and apoptotic effects, increased levels of anti-inflammatory cytokines, decreased pro-inflammatory cytokine production, and induction of regulatory T cell expression. In addition, CB-2 provides a therapeutic target to inhibit inflammatory processes and macrophage migration and to reduce immune-related pathological processes in viral-associated infections. CB-2 affects immune regulation progression, and pro-inflammatory cytokines are elevated in patients with SARS-CoV-2 infection. Thus, it has been reported that CB-2 and SARS-CoV-2 $M^{Pro}$ can be considered as therapeutic targets.

SARS-CoV-2 $M^{Pro}$ is known to play an important role in viral replication of SARS-CoV-2, but an effective target drug or vaccine for SARS-CoV-2 has not yet been developed. There is an urgent need for treatment and prevention of SARS-CoV-2.

On the other hand, cannabinoids (CBDs) bind to the cannabinoid's receptor-2 (CB-2) and act as an agonist to inhibit inflammatory cytokines present at high levels in the patients.

Under this background, the present inventors evaluated binding affinity to SARS-CoV-2 $M^{Pro}$ using AUTODOCK and VINA for compounds or molecules belonging to cannabinoids (CBDs), which are known to reduce inflammation by binding to the cannabinoid receptor-2 (CB-2), and evaluated their conformational stability, and ligand reactivity and stability to SARS-CoV-2 $M^{Pro}$ to select a lead compound or molecule having excellent binding affinity to SARS-CoV-2 $M^{Pro}$. By determining its antiviral effect, the present inventors attempted to determine its potential as a therapeutic agent for severe acute respiratory syndrome coronavirus 2 (SARS-CoV-2).

PRIOR ART DOCUMENTS

Non-Patent Documents

Non-Patent Document 1: Fasinu, P. S., Phillips, S., Elsohly, M. A., and Walker, L. A. (2016). Current status and prospects for cannabidiol preparations as new therapeutic agents. Pharmacotherapy: The Journal of Human Pharmacology and Drug Therapy 36, 781-796.

Non-Patent Document 2: Gurung, A. B., Ali, M. A., Lee, J., Farah, M. A., and Al-Anazi, K. M. (2020). Unravelling lead antiviral phytochemicals for the inhibition of SARS-CoV-2 $M^{Pro}$ enzyme through in silico approach. Life Sciences, 117831.

SUMMARY OF THE DISCLOSURE

Based on the pivotal role in drug targeting of SARS-CoV-2 $M^{Pro}$, the main protease involved in SARS-CoV-2 RNA replication and transcription, the present inventors performed virtual screening on interactions between the SARS-CoV-2 $M^{Pro}$ enzyme and 32 cannabinoids (CBDs) extracted from leaves or unfertilized female flowers of *Cannabis sativa* L. using a density functional theory (DFT) and molecular dynamic simulation. The present inventors have determined that $\Delta^9$-tetrahydrocannabinol ($IC_{50}$=10.25 µM) and cannabidiol ($IC_{50}$=7.91 µM) isolated from the leaves or unfertilized female flowers of *Cannabis sativa* L. of the 32 cannabinoid (CBDs) molecules have stronger antiviral effects against SARS-CoV-2 than the reference drugs lopinavir, chloroquine, and remdesivir ($IC_{50}$ range of 8.16-13.15 µM). In addition, there were $\Delta^9$-Tetrahydrocannabinolic acid, Cannabinol, and Cannabidiolic acid. The present inventors also identified an antiviral effect of $\Delta^9$-Tetrahydrocannabinol or Cannabidiol through an in vitro experiment, and have determined that they may be potential drug candidates for treatment of patients with SARS-CoV-2 infection.

Accordingly, an object of the present invention is to provide an antiviral composition for SARS-CoV-2 comprising an extract of leaves or unfertilized female flowers of *Cannabis sativa* L. or its fraction.

Another object of the present invention is to provide an antiviral composition for SARS-CoV-2 containing cannabinoids as an active ingredient.

In addition, another object of the present invention is to provide a pharmaceutical composition for preventing or treating SARS-CoV-2 infection containing cannabinoids as an active ingredient.

In addition, another object of the present invention is to provide a method for promoting SARS-CoV-2 killing, comprising a step of treating cells with an antiviral composition containing cannabinoids as an active ingredient.

In addition, another object of the present invention is to provide a method for screening an antiviral drug for SARS-CoV-2.

In addition, another object of the present invention is to provide a method for promoting SARS-CoV-2 killing by co-administration of the antiviral composition with one or more drugs selected from the group consisting of lopinavir, chloroquine, and remdesivir.

In addition, another object of the present invention is to provide a pharmaceutical composition for preventing or treating SARS-CoV-2 infection, comprising the antiviral composition and one or more drugs selected from the group consisting of lopinavir, chloroquine, and remdesivir.

In order to solve the above problems, the present invention provides an antiviral composition for SARS-CoV-2 comprising an extract of leaves or unfertilized female flowers of *Cannabis sativa* L. or its fraction.

Further, the present invention provides an antiviral composition for SARS-CoV-2 containing cannabinoids as an active ingredient.

Further, the present invention provides a pharmaceutical composition for preventing or treating SARS-CoV-2 infection containing cannabinoids as an active ingredient.

Further, the present invention provides a method for promoting SARS-CoV-2 killing, comprising a step of treating cells with an antiviral composition containing cannabinoids as an active ingredient.

Further, the present invention provides a method for screening an antiviral drug against SARS-CoV-2.

Further, the present invention provides a method for promoting SARS-CoV-2 killing by co-administration of the antiviral composition with at least one drug selected from the group consisting of lopinavir, chloroquine, and remdesivir.

Furthermore, the present invention provides a pharmaceutical composition for preventing or treating SARS-CoV-2 infection, comprising the antiviral composition and one or more drugs selected from the group consisting of lopinavir, chloroquine, and remdesivir.

The antiviral composition according to the present invention is effective as a therapeutic agent because it has a pronounced proliferation inhibitory effect on SARS-CoV-2 and can alleviate inflammation and fibrosis by attaching to CB-2.

In addition, by using the antiviral composition according to the present invention, it is possible to prevent secondary infection through early treatment of SARS-CoV-2 infection, accelerate the patients' return to society, and minimize economic and industrial losses by preventing damages such as quarantine measures for two weeks of contacts by identifying the movement route of confirmed infectious disease patients and temporary closure of restaurants, business offices, and companies.

DETAILED DESCRIPTION OF THE EMBODIMENTS

Figure 1:
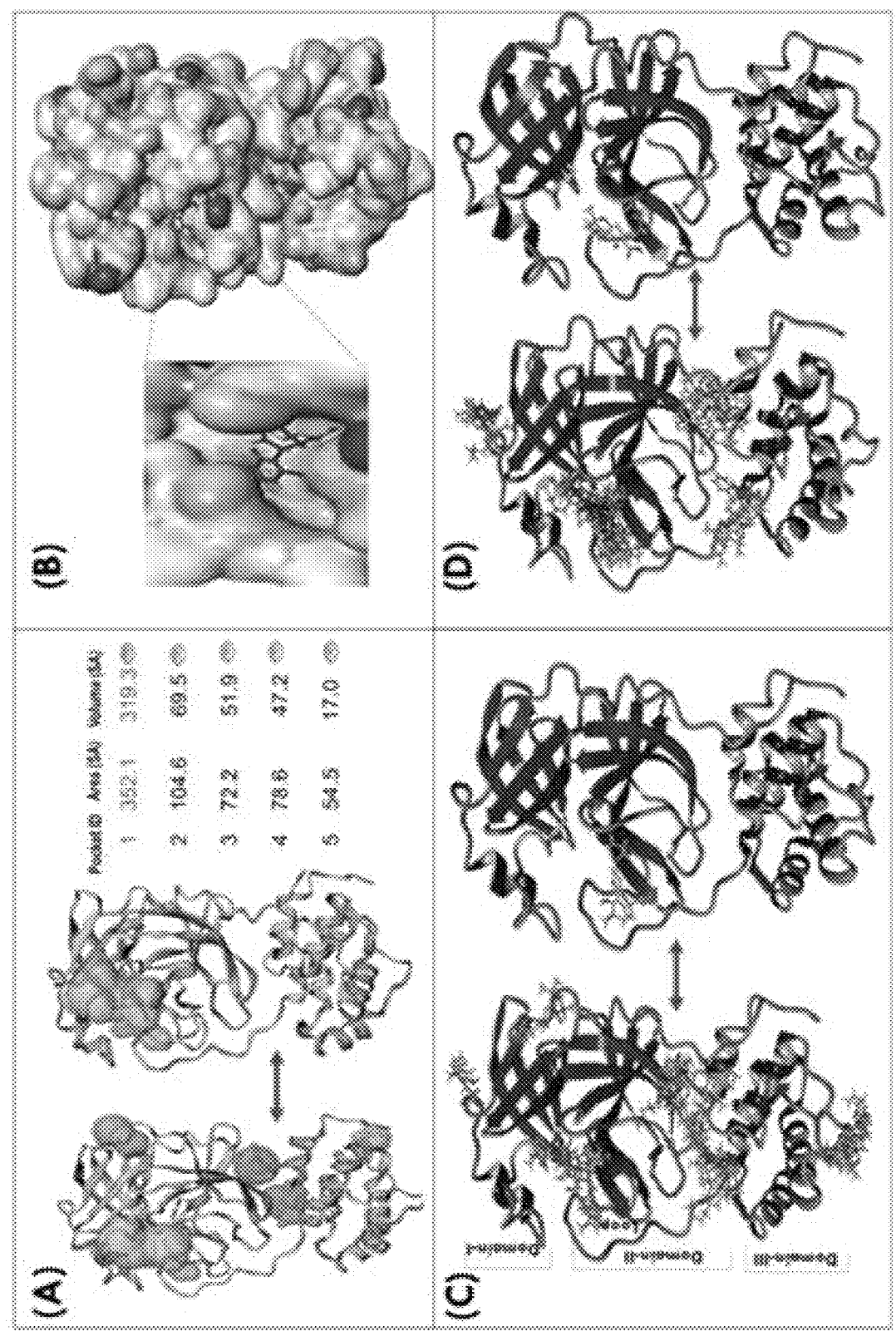
FIG. 1 shows a ribbon structure of SARS-CoV-2 $M^{Pro}$: (A) a ligand binding structure predicted by a CASTp server (http://sts.bioe.uic.edu/castp/index.html); (B) a binding cavity on a hard surface of SARS-CoV-2 $M^{Pro}$; (C) 25 different docking run positions of $\Delta^9$-THC; and (D) CBD complexed with SARS-CoV-2 $M^{Pro}$ similar to pockets predicted by the CASTp server.
Figure 2A:
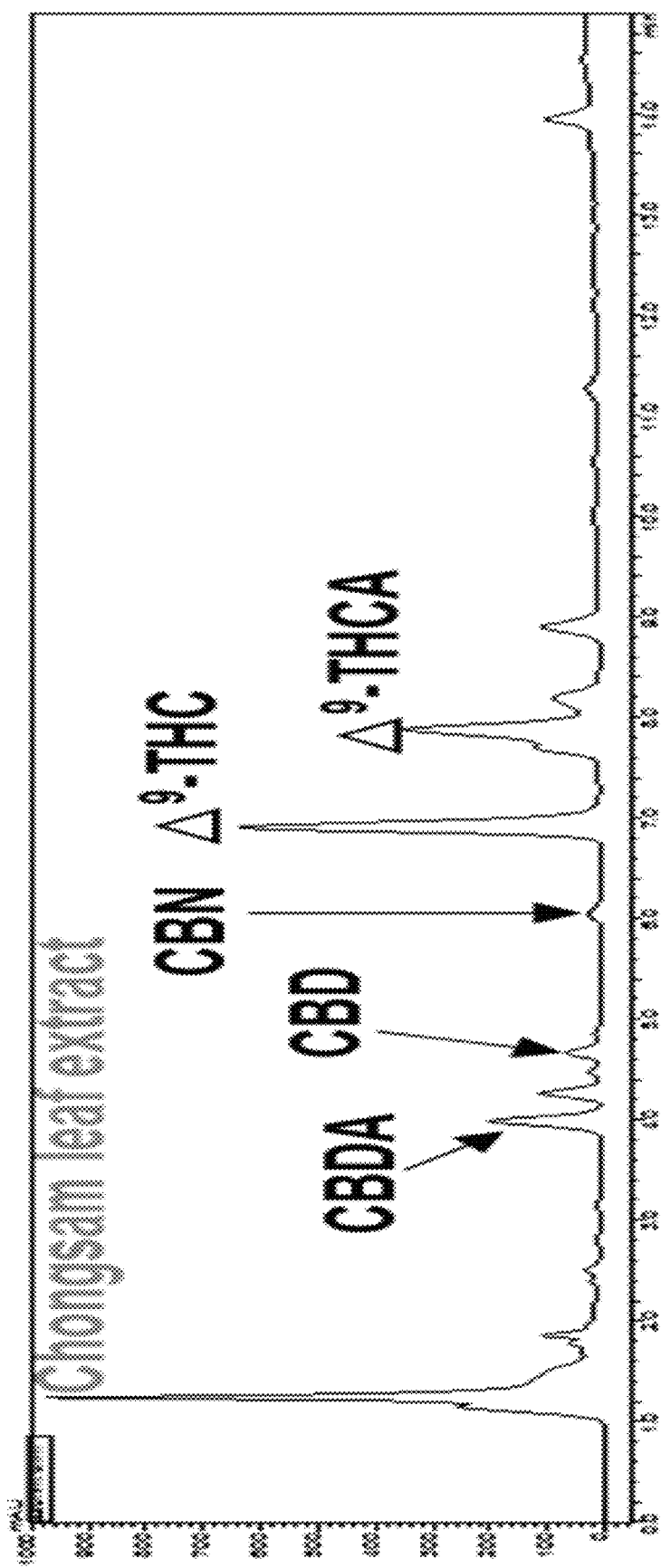
FIGS. 2A-2F show UHPLC chromatogram of an extract of leaves or unfertilized female flowers of *Cannabis sativa* L. and 5 isolated cannabinoid (CBD) molecules.
Figure 2B:
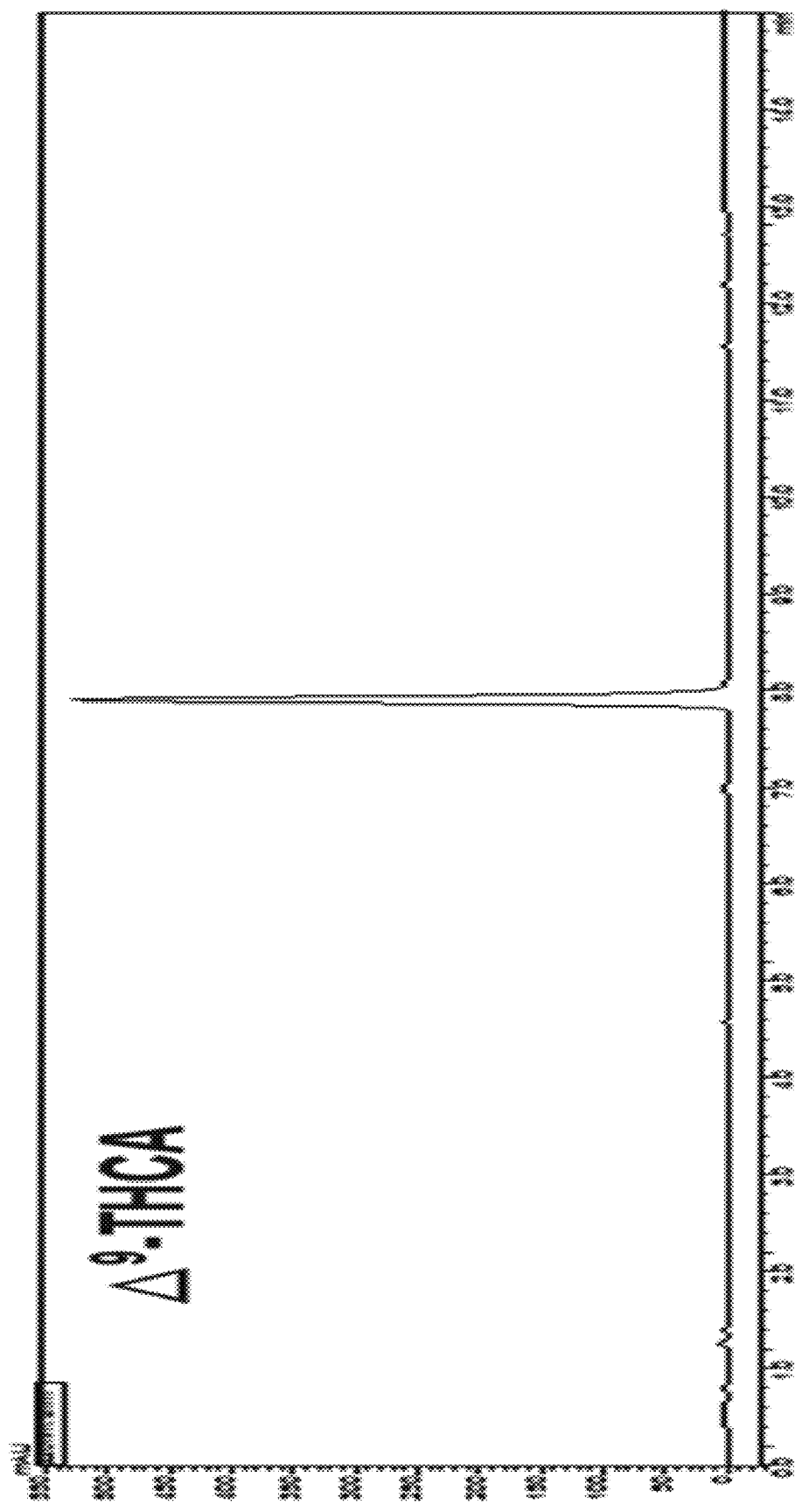
Figure 2C:
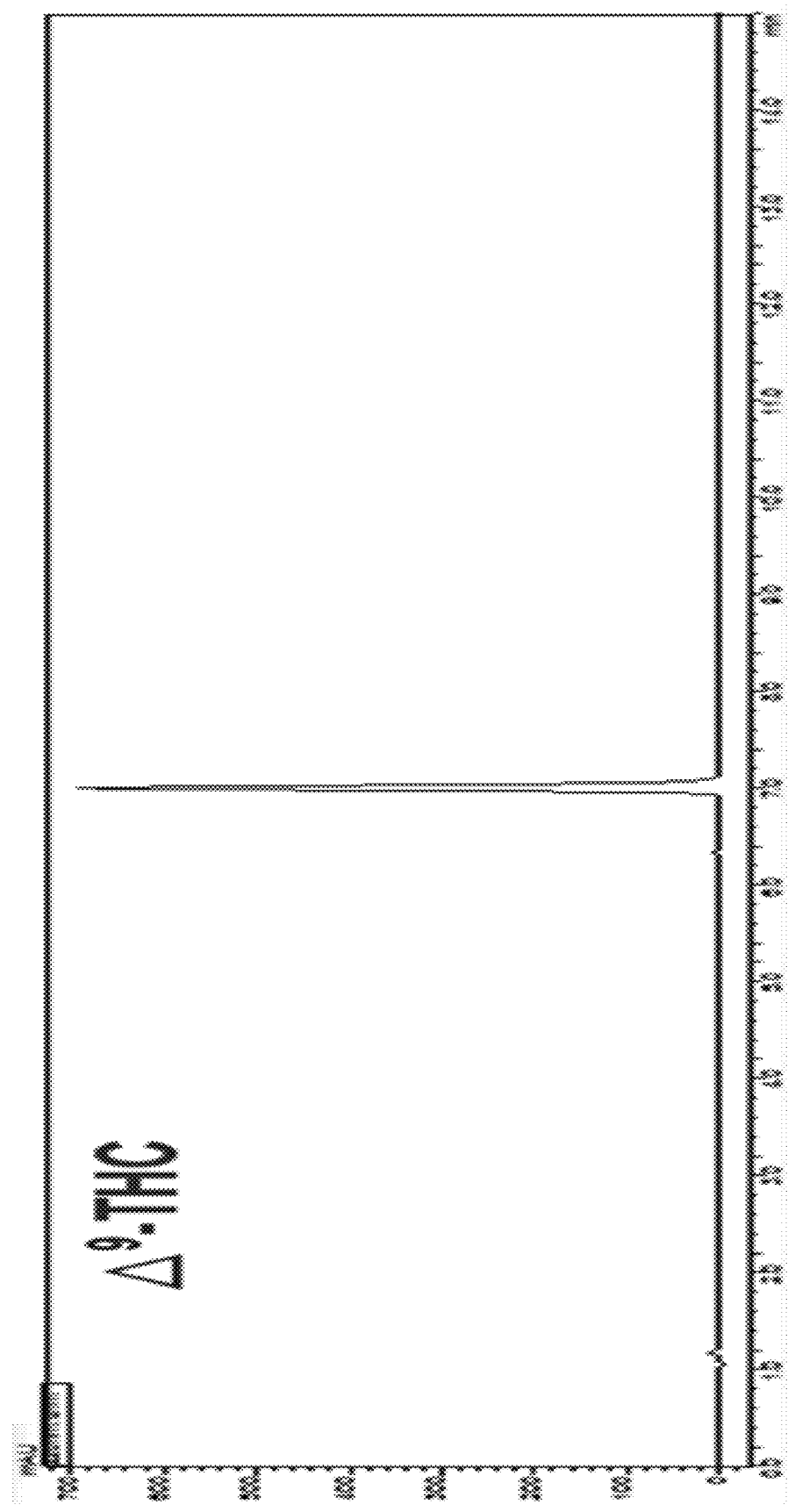
Figure 2D:
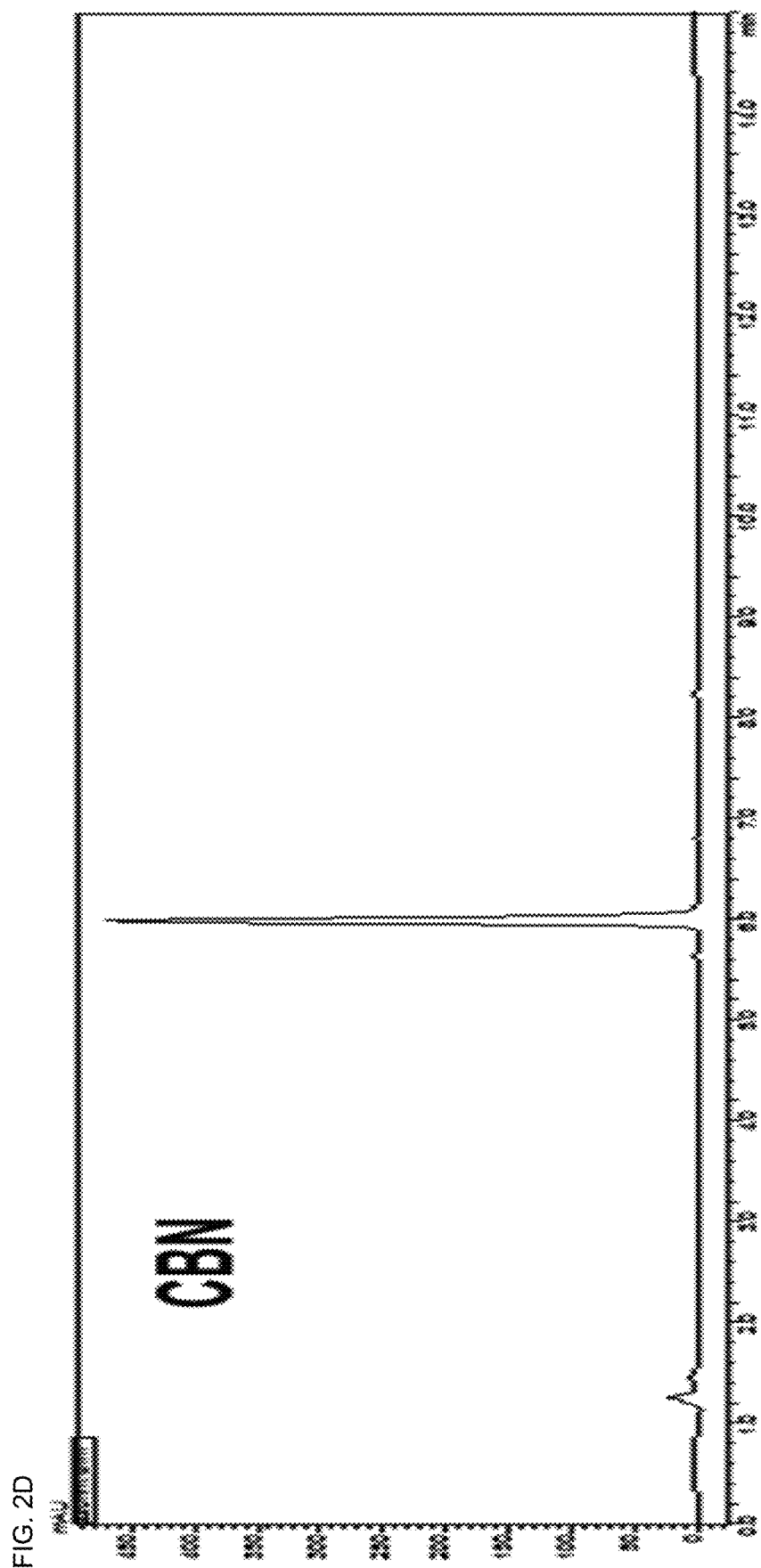
Figure 2E:
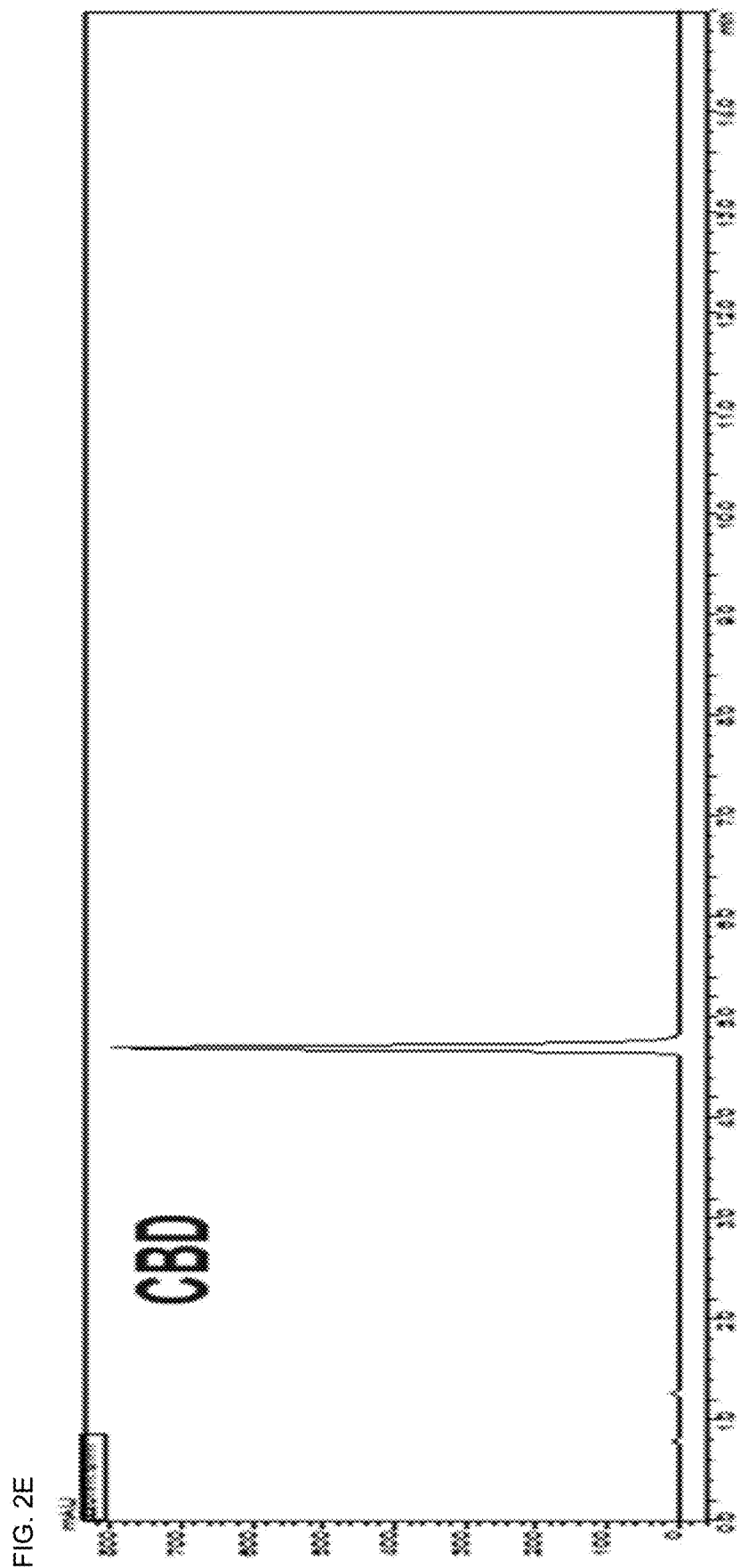
Figure 2F:
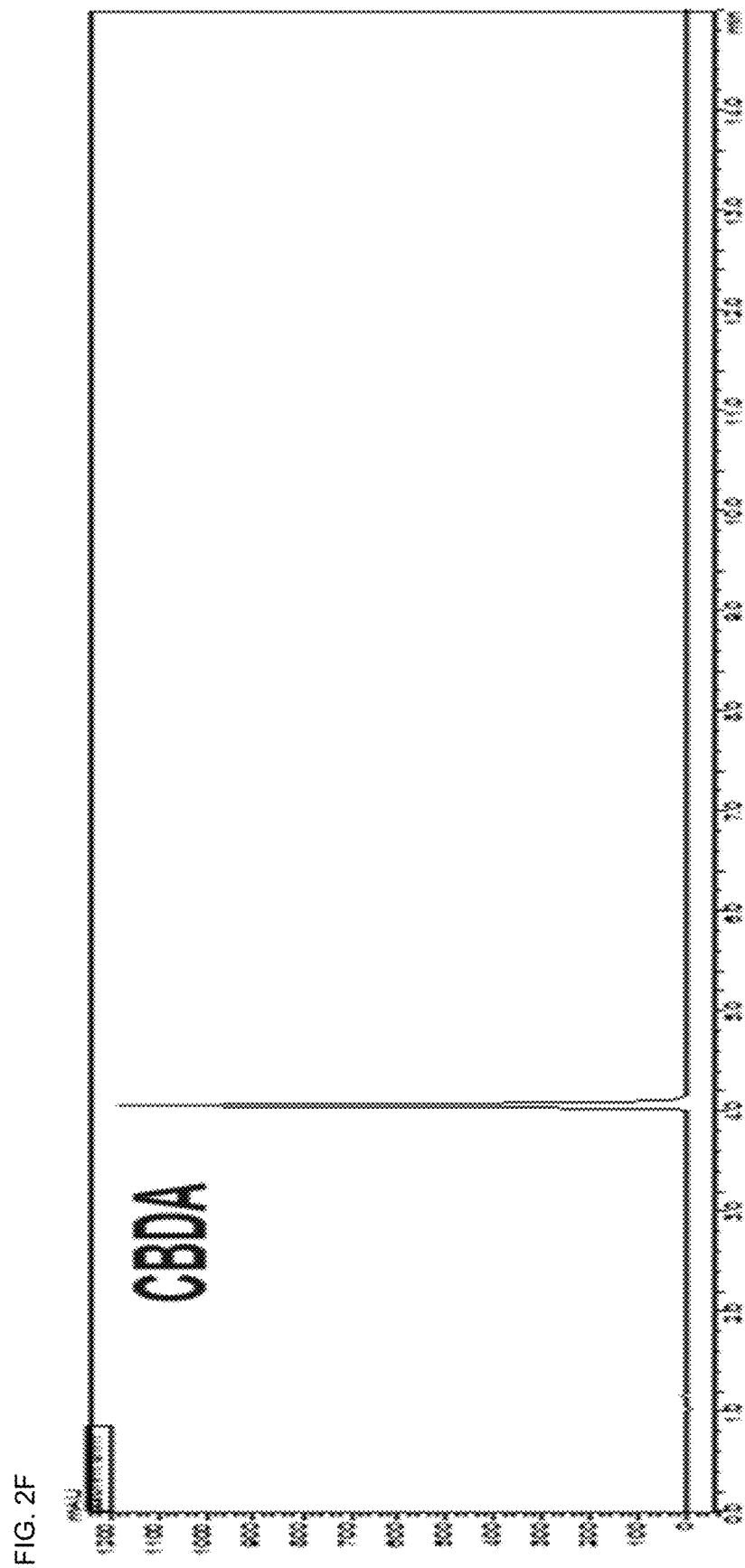

Hereinafter, the present invention will be described in detail.

The present inventors evaluated binding affinity to SARS-CoV-2 $M^{Pro}$ using AUTODOCK and VINA for compounds or molecules belonging to cannabinoids (CBDs), which are known to reduce inflammation by binding to the cannabinoid receptor-2 (CB-2), and evaluated their conformational stability, and ligand reactivity and stability to SARS-CoV-2 $M^{Pro}$ to select a lead compound or molecule having excellent binding affinity to SARS-CoV-2 $M^{pro}$. Then, the present invention was completed by confirming the potential as a SARS-CoV-2 inhibitor by confirming an in vitro antiviral effect of the selected compound or molecule. As a result of the in vitro antiviral test, among 5 molecules belonging to cannabinoids isolated from extracts of leaves or unfertilized female flowers of Cannabis sativa L, Δ⁹-tetrahydrocannabinol (T4) ($IC_{50}$=10.25 μM) and cannabidiol (T22) ($IC_{50}$=7.91 μM) molecules have more excellent binding affinity to SARS-CoV-2 (protease $M^{Pro}$) compared to lopinavir, chloroquine, and remdesivir ($IC_{50}$ range 8.16). Thus, they can act as a SARS-CoV-2 $M^{Pro}$ inhibitor (blocking viral replication). Further, they bind to the cannabinoid receptor-2 (CB-2) that regulates inflammation to reduce pulmonary inflammatory damage. Accordingly, the present inventors confirmed their potential as a therapeutic agent for SARS-CoV-2 infection. In addition, there were Δ⁹-Tetrahydrocannabinolic acid, Cannabinol, and Cannabidiolic acid molecules.

Therefore, the cannabinoids selected according to the present invention are expected to play a leading role in treatment of SARS-CoV-2 infection, either alone or in combination with other drugs.

The present invention provides an antiviral composition for SARS-CoV-2 comprising an extract of leaves or unfertilized female flowers of Cannabis sativa L. or its fraction.

As the leaves or unfertilized female flowers of Cannabis sativa L., those transferred from cannabis growers according to the official procedures after obtaining permission for academic researchers from the Ministry of Food and Drug Safety and Seoul Regional Food and Drug Administration in accordance with the Narcotics Control Act were used.

As used herein, the term "extract" includes any extract of Cannabis sativa L. and products of all formulations that can be formed using the extract such as an extract obtained by extracting the leaves or unfertilized female flowers of Cannabis sativa L., a diluted or concentrated liquid of the extract, a dried product obtained by drying the extract, a roughly purified or purified product of the extract, or a mixture thereof.

A method of extracting the leaves or unfertilized female flowers of Cannabis sativa L. is not particularly limited, and any method commonly used in the art may be used. Non-limiting examples of the extraction method include a hot water extraction method, an ultrasonic extraction method, a filtration method, a reflux extraction method, a supercritical extraction method, and a microwave extraction method, and each of them may be performed alone or two or more methods may be performed together.

According to the present invention, the type of extraction solvent used for extracting the leaves or unfertilized female flowers of Cannabis sativa L. is not particularly limited, and any solvent known in the art may be used. Non-limiting examples of the extraction solvent include water, C1 to C4 alcohols, and mixed solvents thereof, and each of them may be used alone or two or more may be used in combination.

As used herein, the term "fraction" refers to a product obtained by performing fractionation in order to separate a specific component or a specific group of components from a mixture including various components.

The fractionation method for obtaining the fraction in the present invention is not particularly limited, and any method commonly used in the art may be used. Non-limiting examples of the fractionation method include a solvent fractionation method performed by treatment with various solvents, an ultrafiltration fractionation method performed by using an ultrafiltration membrane having a constant molecular weight cut-off value, a chromatographic fractionation method performing various types of chromatography (designed for separation based on size, charge, hydrophobicity, or affinity), and any combinations thereof. For example, a fraction may be obtained from the extract obtained by extracting Cannabis sativa L. according to the present invention by treating the extract with a predetermined solvent.

The extract or fraction may be prepared and used in the form of a dry powder after extraction, but is not limited thereto.

In addition, the present invention provides a method for severe acute respiratory syndrome coronavirus 2 (SARS-CoV-2) comprising, a step of administering to a subject in need thereof an antiviral composition for SARS-CoV-2, including one or more cannabinoids (CBDs) selected from the group consisting of Δ⁹-Tetrahydrocannabinolic acid (Δ⁹-THCA) represented by the following Formula 1, Δ⁹-Tetrahydrocannabinol (Δ⁹-THC) represented by the following Formula 2, Cannabinol (CBN) represented by the following Formula 3, Cannabidiol (CBD) represented by the following Formula 4, and Cannabidiolic acid (CBDA) represented by the following Formula 5.

[Formula 1]

[Formula 2]

[Formula 3]

[Formula 4]

[Formula 5]

The cannabinoids (CBDs) may be derived from the extract of leaves or unfertilized female flowers of *Cannabis sativa* L. or its fraction.

The cannabinoids (CBDs) bind to GLN189, MET165, and GLU166 residues in SARS-CoV-2 $M^{Pro}$ protease to inhibit protease action.

Further, the present invention provides a pharmaceutical composition for preventing or treating SARS-CoV-2 infection including the antiviral composition as an active ingredient. $\Delta^9$-Tetrahydrocannabinolic acid ($\Delta^9$-THCA), $\Delta^9$-Tetrahydrocannabinol ($\Delta^9$-THC), Cannabinol (CBN), Cannabidiol (CBD), and Cannabidiolic acid (CBDA) belonging to Cannabinoids (CBDs) bind to the cannabinoid's receptor-2 (CB-2) and act as an agonist, thereby inhibiting inflammatory cytokines by attaching to the CB-2 receptor to alleviate inflammation and fibrosis.

In addition, the present invention provides a method for preventing or treating severe acute respiratory syndrome coronavirus 2 (SARS-CoV-2) infection comprising, a step of administering to a subject in need thereof a pharmaceutical composition for prevention or treatment of SARS-CoV-2 infection including the antiviral composition; and one or more drugs selected from the group consisting of lopinavir, chloroquine, and remdesivir.

The lopinavir is an existing HIV treatment agent, chloroquine is an antimalarial agent, and remdesivir is a drug known as an antiviral agent developed as a treatment for Ebola.

The pharmaceutical composition may further include one or more additives selected from the group consisting of carriers, excipients, disintegrants, sweeteners, coating agents, blowing agents, lubricants, glidant agents, flavoring agents, antioxidants, buffers, bacteriostatic agents, diluents, dispersants, surfactants, binders, and lubricants commonly used in preparation of pharmaceutical compositions.

More specifically, the carrier, the excipient, and the diluent may include lactose, dextrose, sucrose, sorbitol, mannitol, xylitol, erythritol, maltitol, starch, gum acacia, alginate, gelatin, calcium phosphate, calcium silicate, cellulose, methyl cellulose, microcrystalline Cellulose, polyvinyl pyrrolidone, water, methylhydroxybenzoate, propylhydroxybenzoate, talc, magnesium stearate, and mineral oil. Examples of solid preparations for oral administration include tablets, pills, powders, granules, and capsules, and these solid preparations may be prepared by mixing at least one excipient such as starch, calcium carbonate, sucrose or lactose, and gelatin, in the composition. In addition to the excipients, lubricants such as magnesium stearate and talc can also be used. Examples of liquid preparations for oral use include suspensions, solutions, emulsions, and syrups, and the liquid preparations may contain various excipients such as wetting agents, sweeteners, fragrances, and preservatives, in addition to water and liquid paraffin, which are commonly used simple diluents. Examples of preparations for parenteral administration include sterile aqueous solutions, non-aqueous solutions, suspensions, emulsions, freeze-dried preparations, and suppositories. The non-aqueous solvents and suspensions may include propylene glycol, polyethylene glycol, vegetable oils such as olive oil, and injectable esters such as ethyl oleate. As a base material for the suppositories, witepsol, macrogol, tween 61, cacao butter, laurin, glycerogelatin, and the like can be used.

In addition, the pharmaceutical composition can be formulated and used as granules, powders, coated tablets, tablets, pills, capsules, suppositories, gels, syrups, juices, suspensions, emulsions, drops, or liquids according to conventional methods. The pharmaceutical composition may be administered to a subject in a conventional manner via intravenous, intraarterial, intraperitoneal, intramuscular, intraarterial, intraperitoneal, intrasternal, transdermal, intranasal, inhalation, topical, rectal, oral, intraocular, or intradermal routes.

Preferred dosage of the cannabinoids (CBDs) may vary depending on the condition and weight of the subject, the type and extent of the disease, the drug form, and the route and duration of administration, and may be appropriately selected by those skilled in the art. According to an embodiment of the present invention, the daily dose may be 0.01 to 75 mg, more specifically, 10 to 75 mg, but is not limited thereto. CBDs may be administered once a day or in several divided doses, but the scope of the present invention is not limited thereto.

In addition, the present invention provides a method for promoting SARS-CoV-2 killing, comprising a step of treating cells with a solution containing the antiviral composition as an active ingredient.

In addition, the present invention provides a method for promoting SARS-CoV-2 killing including administering the antiviral composition in combination with one or more drugs selected from the group consisting of lopinavir, chloroquine, and remdesivir.

In addition, the present invention provides a method for screening an antiviral drug for SARS-CoV-2, including (a) selecting drug candidates which binds to GLN189, MET165, and GLU166 residues in SARS-CoV-2 $M^{Pro}$ protease, and (b) comparing the drug candidates of the step (a) and control material to select again a drug candidate with superior molecular binding affinity (kcal/mol).

The control material may be at least one selected from the group consisting of lopinavir, chloroquine, and remdesivir, but is not necessarily limited thereto.

In addition, the present invention provides a method of preventing or treating severe acute respiratory syndrome coronavirus 2 (SARS-CoV-2) infection comprising, a step of administering to a subject in need thereof a pharmaceutical composition comprising the antiviral composition and one or more drugs selected from the group consisting of lopinavir, chloroquine, and remdesivir.

Therefore, the antiviral composition according to the present invention has a pronounced proliferation inhibitory effect on SARS-CoV-2 and is attached to cannabinoid receptor-2 (CB-2) to relieve inflammation and fibrosis. Thus, the antiviral composition can be used widely as a treatment for SARS-CoV-2 because it is effective in both suppressing virus proliferation and treating inflammation such as cytokine storms.

Hereinafter, in order to help understanding of the present invention, exemplary embodiments will be described in detail. However, the following embodiments are merely illustrative of the present invention, and the scope of the present invention is not limited to the embodiments. The embodiments of the present invention are provided to more completely explain the present invention to those skilled in the art.

EXPERIMENTAL EXAMPLES

The following experimental examples are intended to provide experimental examples commonly applied to each embodiment according to the present invention.

<Materials and Methods>

1. Collection of SARS-CoV-2 $M^{Pro}$ Protein. And Ligand

Active sites were predicted using the CASTp server (http://sts.bioe.uic.edu/) for virtual screening. Target proteins were prepared and purified using Protein preparation wizards from Schrodinger's suite.

Excess co-crystallizing water molecules were removed and an appropriate number of hydrogen atoms were added. 2D structures of 32 cannabinoids (CBDs) were downloaded from PubChem (https://pubchem.ncbi.nlm.nih.gov/) in simulation description format (SDF).

2. Preparation of Ligands and Structure-Based Virtual Screening

Cannabinoids (CBDs) were prepared using the LigPrep tool from Schrodinger's suite and optimized to minimum energy using a density functional approach. An OPLS 2005 force field was used to improve and minimize the bond sequence and conformation. This prepared ligand library was received through structure-based virtual screening, and the active site of SARS-CoV-2 $M^{Pro}$ was predicted using the CASTp server.

The active pocket of SARS-CoV-2 $M^{Pro}$ was found by executing VINA 25 times together with SARS-CoV-2 $M^{Pro}$ (FIG. 1).

Molecular conformational stability at the predicted active site could be confirmed through the site predicted by the CASTp server. The ligand was treated as a rigid entity, while the receptor was treated as a flexible entity.

The docking study used two docking programs to ensure reliability, validity, and reproducibility of the results. More specifically, using the docking program AUTODOCK (Journal of computer-aided molecular design 24, 417-422) and VINA (Journal of computational chemistry 31, 455-461), the binding energy and interactions between cannabinoids (CBDs) and SARS-CoV-2 $M^{Pro}$ were analyzed using a computational approach (Journal of computer-aided molecular design 24, 417-422). In addition, BIOVIA Discovery Studio Visualizer was used to visualize the interactions of cannabinoids (CBDs) with proteins.

3. Molecular Dynamics (MD) Simulation and Energy Calculation

For $\Delta^9$-THCA, $\Delta^9$-THC, CBN, CBD, and CBDA of the five molecules belonging to cannabinoids (CBDs) isolated from the leaves of *Cannabis sativa* L., stability of the docking conformation for SARS-CoV-2 $M^{Pro}$ was examined. More specifically, as a molecular dynamics simulation, YASARA dynamic software using SAMSUNG Intel® Core™ i5-CPU, 4 GB RAM system, Windows 7 enterprise version (64) was used.

At this time, the best docking binding conformation of the cannabinoid complex was evaluated through binding stability to SARS-CoV-2 $M^{Pro}$ A simulated cell of the cannabinoid complex was defined using periodic cell boundaries and filled with water solvent at a density of 0.997 g/L. The cell boundary size of the periodic simulation for the whole system was set to X=61.30 A°, Y=82.84 A°, and Z=52.14 A°. Sodium and chloride ions were randomly placed to neutralize the charge. Pka values were predicted only for the side chains of Asp, Glu, His, and Lys residues.

An AMBER14 molecular dynamic force field was selected through MD simulation under physiological conditions of 298K, pH 7.4, and 0.9% NaCl. The system energy initially minimized the steep descent followed by the procedures as described above.

The MD simulation over 20 ns was performed at constant temperature and pressure, and molecular docking (MD) trajectories were stored for 250 ps for further analysis. The molecular docking (MD) trajectories were analyzed using the YASARA template file ("md_analysis.mcr"). In addition, the binding energy conformation of the complex was analyzed using another YASARA template file ("md_analyzebindenergy.mcr").

The average conformational stability of the model was estimated through simulation and root mean square deviation (RMSD). According to the YASARA manual, the free binding energy is calculated without entropy intervention as follows. Since YASARA provides positive binding energy, more positive energy indicates favorable binding to the receptor in the selected force field, whereas negative binding energy indicates weak binding.

Orbital analysis data obtained by the molecular docking (MD) simulation was acquired using SigmaPlot 10.0 (SigmaPlot, 2006). The CBD/SARS-CoV-2 M$^{Pro}$ binding conformation was visualized using Discovery Studio visualization software.

4. Structural Stability of Cannabinoids (CBDs) Determined by Density Functional Theory (DFT)

Frontier molecular orbitals (FMO), i.e. HOMO (highest occupied molecular orbitals) and LUMO (least unoccupied molecular orbitals), were evaluated using the density functional theory (DFT).

HOMO and LUMO of A9-THCA, Δ$^9$-THC, CBN, CBD, and CBDA were determined, and a HOMO-LUMO energy gap was calculated using the following Equation 1.

$$\Delta E = E_{LUMO} - E_{HOMO}. \quad \text{[Equation 1]}$$

Chemical potentials (μ) and chemical hardnesses (η) were calculated using energies associated with HOMO and LUMO.

$$\mu = \frac{ELUMO + EHOMO}{2} \quad \text{[Equation 2]}$$

$$\eta = \frac{ELUMO - EHOMO}{2} \quad \text{[Equation 3]}$$

Electronegativity (χ) and electrophilicity (ω) were calculated using ionization potentials (1) generally defined as negative EHOMO values. In addition, electron affinities (A) were defined to be equal to negative ELUMO values.

$$\omega = \frac{\mu 2}{2\eta} \quad \text{[Equation 4]}$$

5. Experimental Procedure for Extraction of Cannabinoids (CBDs)

Preparative HPLC was performed on an LC-Forte/R (YMC, USA) equipped with an ultraviolet detector (220 nm) using a Phenomenex Luna C18 column (250×21.2 mm, 10 μm), and semi-preparative LC (Gilson, USA) was performed using a refractive index (RI) detector and a Phenomenex Luna C18(2) column (250×10 mm, 5 μm).

NMR spectra were recorded in chloroform-d using a Varian Superconducting FT-NMR System (operated at 500 and 125 MHz for $^1$H and $^{13}$C, respectively). Chemical shifts of protons and carbon spectra were observed in chloroform-d, and residual solvent peaks appeared at 7.26 ppm and 77.0 ppm, respectively.

Ultra-high performance liquid chromatography (UPLC) ESI mass spectrometry was performed using a Shimadzu LCMS-2020 system. Chongsam (Korean hemp, *Cannabis sativa* L.) was obtained from the Association (Andong-si, Gyeongsangbuk-do, Korea) according to the transfer approval procedure (approval number 1564) prescribed by the Ministry of Food and Drug Safety and the Seoul Regional Food and Drug Administration. Chongsam leaves were harvested in July 2019, dried naturally, chopped, extracted twice with ethanol (200 ml) at room temperature, and filtered. The ethanol extract thus obtained (1.64 g) was suspended in water and then successively fractionated with hexane to obtain 720 mg of a residue.

Silica open column chromatography (Merck, 230-400 mesh, 2.0×10.0 cm ID) was performed using a hexane:ethyl acetate step gradient (F1-10:0, F2-25:1, F3-10:1 and F4-0; each 200 ml). The F2 (187 mg) fraction was purified by preparative HPLC (Phenomenex Luna C18 column; 250× 21.2 mm, 10 μm) using a gradient system of water (A) and MeCN (B) (70-85% MeCN over 60 min). At this time, four sub-fractions (a-d) were obtained at a flow rate of 10 ml/min using a 220 nm UV detector. Further purification for each subfraction was performed on semi-preparative HPLC (Phenomenex Luna C18 (2); 250×10 mm, 5 μm) using 70-85% MeCN eluent at a flow rate of 4 ml/min. Pure compounds Δ$^9$-THCA (17.0 mg), Δ$^9$-THC (48 mg), CBN (1.1 mg), and CBD (1.9 mg) were obtained (FIGS. 2A-2F).

To obtain another cannabinoid, CBDA, the fraction F3 (35 mg) was gradient eluted over 60 min with water (A) and 65-80% MeCN (B) at a rate of 10 ml/min using the 220 nm UV detector and extracted by preparative HPLC (Phenomenex Luna C18 column; 250×21.2 mm, 10 μm). Next, pure CBDA (7.9 mg) was obtained by purification using semi-preparative HPLC (Phenomenex Luna C18 (2); 250×10 mm, 5 μm) using a 65-80% MeCN gradient at a flow rate of 4 ml/min. Five isolated compounds were identified by comparing the NMR spectral results with previously reported literature (The Journal of Organic Chemistry 57, 3627-3631; An International Journal of Plant Chemical and Biochemical Techniques 15, 345-354).

6. Cannabinoids (CBDs) Analysis

For qualitative and/or quantitative analysis, a reversed-phase anaysis Shimadzu Nexera X2 UHPLC system (SPD-M20A) including a solvent degasser (DGU-20A), a binary pump (LC-30AD), an autosampler (SIL-30AC), a system controller device (CBM-20A), and a photodiode array detector, and a column oven (CTO-20AC) were used. For qualitative analysis, ESI-MS (Electrospray ionization (ESI)-mass spectrometry (MS)) was performed using a Shimadzu LCMS-2020 system. A Phenomenex Luna Omega polar C18 column (150×2.1 mm, 1.6 μm) was used. The mobile phase was tested with a binary gradient of solvent A (water) and solvent B (acetonitrile) as follows (initial: 70% B, 10.0 min: 85% B, 11.0 min: 95% B, and 15.0 min: 70% B). At this time, the flow rate was set to 0.3 mL/min, and the detection wavelength was 220 nm.

7. Confirmation of In Vitro Antiviral Activity of Cannabinoids (CBDs) on SARS-CoV-2

The antiviral activity of cannabinoids (CBDs) was determined by a conventionally known method (Jeon, S., Ko, M., Lee, J., Choi, I., Byun, S Y, Park, S., Shum, D., and Kim, S. (2020). Identification of antiviral drug candidates against SARS-CoV-2 from FDA-approved drugs. Antimicrobial Agents and Chemotherapy).

More specifically, images of viral N protein and cell nuclei were analyzed using a confocal microscope using Mining (IM) software. A dose-response curve (DRC) was generated for each compound, and Vero cells were obtained from the American Type Culture Collection (ATCC CCL-81) for in vitro drug screening assays. The cells were placed in Dulbecco's Modified Eagle's Medium (DMEM; Welgene) containing 1×Antibiotic-Antimycotic solution (Gibco) and heat-inactivated fetal bovine serum (FBS) at 37° C. and 5% CO$_2$ atmosphere. SARS-CoV-2 (βCoV/KOR/KCDC03/2020) was provided by the Korea Centers for Disease Control and Prevention (KCDC), and SARS-CoV-2 virus was propagated in the Vero cells. In addition, virus titers were measured by performing Vero cells plaque assays. Institut Pasteur Korea supported this study based on Biosafety Level 3 (BSL-3) control procedures in laboratories approved for use by the Centers for Disease Control and Prevention (KCDC) in accordance with the rules issued by the National Institute of Health (KNIH).

8. Drugs and Reagents

Cannabinoids (CBDs) obtained through the extraction and purification as described above were used. Remdesivir (HY-104077), lopinavir (LPV; S1380), and chloroquine were purchased from MedChemExpress (Monmouth Junction, N.J.), SelleckChem (Houston, Tex.), and Sigma-Aldrich (St. Louis, Mo.), respectively. Anti-SARS-CoV-2 N protein antibody was purchased from Sino Biological Inc. (Beijing, China), and Hoechst 33342 and Alexa Fluor 488 goat anti-rabbit IgG (H+L) secondary antibody were purchased from Molecular Probes. In addition, normal goat serum and paraformaldehyde (PFA) (32% aqueous solution) were purchased from Vector Laboratories, Inc. (Burlingame, Calif.) and Electron Microscopy Sciences (Hatfield, Pa.), respectively.

9. Dose-Response Curve (DRC) Analysis Determined by Immunofluorescence

Dose-response curve (DRC) analysis was performed according to a conventionally known method (Jeon, S., Ko, M., Lee, J., Choi, I., Byun, S Y, Park, S., Shum, D., and Kim, S. (2020). Identification of antiviral drug candidates against SARS-CoV-2 from FDA-approved drugs. Antimicrobial Agents and Chemotherapy). Briefly, the Vero cells were seeded at $1.2\times10^4$ cells per well in DMEM containing 1× Antibiotic-Antimycotic solution (Gibco) and 2% FBS in a 384-well, μClear plate (Greiner Bio-One) and maintained for 24 h. After that, the cells were treated twice with compounds in the concentration range of 0.05-100 μM. A 9-point dose-response curve (DRC) was generated. For viral infection, the plate was transferred to a BSL-3 isolation facility and SARS-CoV-2 was added to an MOI value of 0.0125. Next, the cells were fixed at 24 hpi with 4% PFA and measured using the immunofluorescence method Operetta (Perkin Elmer).

Images acquired using software within the Pasteur Institute in Korea were used to estimate the infection rate and cell number, and antiviral activity was normalized to negative (0.5% DMSO) and positive controls (mock). The dose-response curve (DRC) was measured using the sigmoidal dose-response model $Y=Bottom+(Top-Bottom)/(1+(IC_{50}/X)^{Hillslope})$ using Prism or 7XLfit 4 software. Finally, $IC_{50}$ values were measured for curves fitted to the normalized activity data set. The $IC_{50}$ and $CC_{50}$ values were measured in duplicate, and the quality of each analysis was verified using the coefficient of variation (% CV) and Z'-factors.

10. Identification of Isolated Cannabinoids (CBDs) Through Analytical Techniques 1) $\Delta^9$-Tetrahydrocannabinolic acid ($\Delta^9$-THCA)

$^1$H NMR (500 MHz, CDCl$_3$, CHCl$_3$=7.26): 612.20 (1H, brs), 6.39 (1H, s), 6.26 (1H, s), 3.23 (1H, d, J=8.4 Hz), 2.98-2.93 (1H, m), 2.81-2.76 (1H, m), 2.18-2.17 (2H, m), 1.94-1.91 (1H, m), 1.71-1.68 (1H, m), 1.68 (3H, s), 1.56-1.58 (2H, m), 1.47-1.41 (1H, m), 1.44 (3H, s), 1.38-1.34 (4H, m), 1.11 (3H, s), 0.90 (3H, t, J=5.2 Hz). $^{13}$C NMR (125 MHz, CDCl$_3$, CDCl$_{3=77.00}$): δ 176.2, 164.7, 159.7, 147.0, 133.9, 123.5, 112.6, 109.8, 102.3, 78.8, 45.6, 36.5, 33.4, 32.0, 31.3, 31.2, 27.4, 25.0, 23.3, 22.5, 19.5, 14.1. LRMS (ESI) m/z calcd for $C_{22}H_{29}O_4$ 357.21 (M-H)$^-$, found 357.20.

2) $\Delta^9$-Tetrahydrocannabinol ($\Delta^9$-THC)

$^1$H NMR (500 MHz, CDCl$_3$, CHCl$_3$=7.26): 66.30 (1H, s), 6.27 (1H, s), 6.14 (1H, s), 4.78 (1H, s), 3.20 (1H, d, J=8.4 Hz), 2.43 (2H, td, J=6.4 and 2.0 Hz), 2.17-2.15 (2H, m), 1.94-1.88 (1H, m), 1.71-1.67 (1H, m), 1.68 (3H, s), 1.55 (2H, q, J=6.0 Hz), 1.44-1.37 (1H, m), 1.41 (3H, s), 1.32-1.24 (4H, m), 1.09 (3H, s), 0.87 (3H, t, J=5.6 Hz). $^{13}$C NMR (125 MHz, CDCl$_3$, CDCl$_3$=77.00): δ 154.7, 154.1, 142.8, 134.4, 123.7, 123.6, 110.1, 109.0, 107.5, 45.8, 35.5, 33.5, 31.5, 31.1, 30.7, 27.5, 25.0, 23.4, 22.5, 19.3, 14.0. LRMS (ESI) m/z calcd for $C_{21}H_{29}O_2$ 313.22 (M-H)$^-$, found 313.20.

3) Cannabinol (CBN)

$^1$H NMR (500 MHz, CDCl$_3$, CHCl$_3$=7.26): 58.17 (1H, s), 7.16 (1H, d, J=6.0 Hz), 7.08 (1H, d, J=6.0 Hz), 6.45 (1H, s), 6.30 (1H, s), 5.18 (1H, brs), 2.51 (2H, t, J=6.4 Hz), 2.40 (3H, s), 1.64-1.57 (2H, m), 1.61 (6H, s)), 1.36-1.26 (4H, m), 0.90 (3H, t, J=6.0 Hz). $^{13}$C NMR (125 MHz, CDCl$_3$, CDCl$_{3=77.00}$): δ 154.6, 153.0, 144.5, 136.9, 136.8, 127.6, 127.5, 126.3, 122.6, 110.8, 109.8, 108.6, 77.3, 35.6, 31.4, 30.5, 27.1, 27.1, 22.5, 21.5, 14.0. LRMS (ESI) m/z calcd for $C_{21}H_{25}O_2$ 309.19 (M-H)$^-$, found 309.20.

4) Cannabidiol (CBD)

$^1$H NMR (500 MHz, CDCl$_3$, CHCl$_3$=7.26): 66.28 (1H, brs), 6.16 (1H, brs), 5.99 (1H, brs), 5.57 (1 H, s), 4.66 (2H, s), 4.55 (1H, s), 3.86-3.83 (1H, m), 2.43 (2H, t, J=6.0 Hz), 2.39 (1H, td, J=8.8 and 2.0 Hz), 2.27-2.20 (1H, m), 2.12-2.07 (1H, m), 1.86-1.73 (2H, m), 1.79 (3H, s), 1.65 (3H, s), 1.55 (2H, q, J=6.0 Hz), 1.35-1.23 (4H, m), 0.87 (3H, t, J=6.0 Hz). $^{13}$C NMR (125 MHz, CDCl$_3$, CDCl$_3$=77.00): 5149.4, 149.4, 143.0, 140.1, 124.1, 113.7, 110.8, 110.8, 109.8, 107.9, 46.1, 37.2, 35.5, 31.5, 30.6, 30.4, 28.4, 23.7, 22.5, 20.5, 14.0. LRMS (ESI) m/z calcd for $C_{21}H_{29}O_2$ 313.22 (M-H)$^-$, found 313.20.

5) Cannabidiolic acid (CBDA)

$^1$H NMR (500 MHz, CDCl$_3$, CHCl$_3$=7.26): 511.85 (1H, s), 6.68 (1H, s), 6.28 (1H, s), 5.58 (1H, s), 4.56 (1H, s), 4.40 (1H, s), 4.12-4.10 (1H, m), 3.10-2.90 (1H, m), 2.86-2.82 (1H, m), 2.41-2.38 (1H, m), 2.26-2.22 (1H, m), 2.12 (1H, d, J=14.0 Hz), 1.87-1.76 (2H, m), 1.81 (3H, s), 1.73 (3H, s), 1.60-1.58 (2H, m), 1.36-1.34 (4H, m), 0.91 (3H, t, J=6.0 Hz). $^{13}$C NMR (125 MHz, CDCl$_3$, CDCl$_3$=77.00): δ 176.5, 164.2, 161.0, 147.7, 147.1, 140.5, 123.8, 114.4, 112.0, 111.3, 102.5, 46.6, 36.6, 35.3, 31.9, 31.2, 30.1, 27.7, 23.7, 22.5, 18.8, 14.1. LRMS (ESI) m/z calcd for $C_{22}H_{29}O_4$ 357.21 (M-H)$^-$, found 357.20.

<Example 1> Identification of Molecular Docking and Molecular Interaction Mapping Between SARS-CoV-2 M$^{Pro}$ and Cannabinoids (CBDs)

To investigate a molecular interaction between cannabinoids (CBDs) and SARS-CoV-2 M$^{Pro}$, a virtual screening of 32 known cannabinoids (CBDs) was performed (Table 1). Table 1 shows the molecular binding affinities of CBDs (T1-T32) and positive controls ($C_1$-$C_5$) to SARS-CoV-2 M$^{Pro}$ TABLE 1
| Groups | Chemical Structure | PubChem Ids (Compounds) | Binding energy (kcal/mol) VINA | Binding energy (kcal/mol) AUTODOCK |
|---|---|---|---|---|
| C1 | 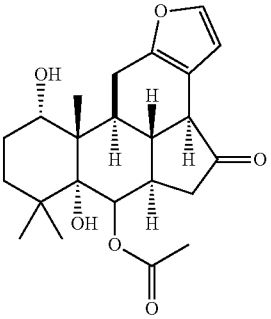 | 10835061 (Bonducellpin D) | −7.09 | −9.75 |
| C2 | 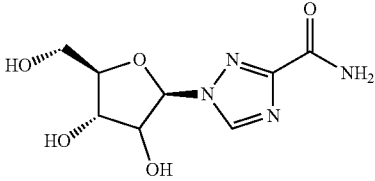 | 37542 (Ribavirin) | −4.97 | −7.21 |
| C3 | 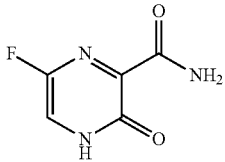 [SMILES: NC(=O)c1nc(F)c[nH]c1=O] | 492405 (Favipiravir) | −4.97 | −4.76 |
| C4 | 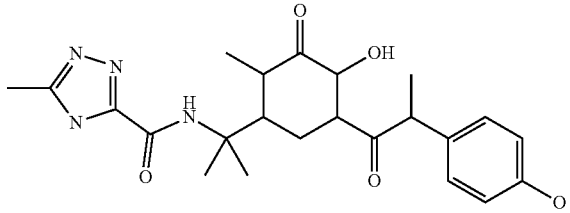 [SMILES: Cc1nnc(C(=O)NC(C)(C)C2CC(C(=O)C(C)c3ccc(O)cc3)C(O)C(=O)C2C)[nH]1] | 54671008 (Raltegravir) | −7.52 | −9.55 |
| C5 | 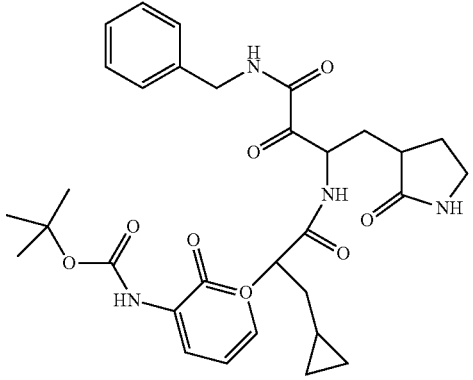 | α-Ketoamide 13b | −7.11 | −9.50 |

TABLE 1-continued

| Groups | Chemical Structure | PubChem Ids (Compounds) | Binding energy (kcal/mol) VINA | Binding energy (kcal/mol) AUTODOCK |
| --- | --- | --- | --- | --- |
| T1 | 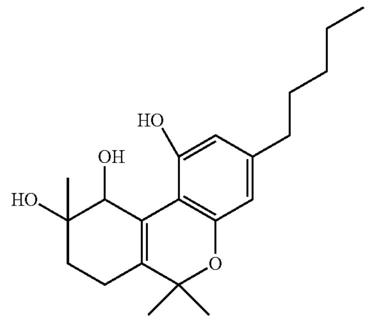 [SMILES: CCCCCc1cc(O)c2c(c1)OC(C)(C)C1=C2C(O)C(C)(O)CC1] | 11551959 (Cannabitriol) | −7.62 | −10.36 |
| T2 | 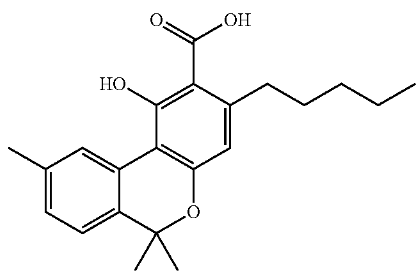 [SMILES: CCCCCc1cc2c(c(O)c1C(=O)O)-c1cc(C)ccc1C(C)(C)O2] | 3081990 (Cannabinolic acid) | −7.59 | −10.70 |
| T3 | 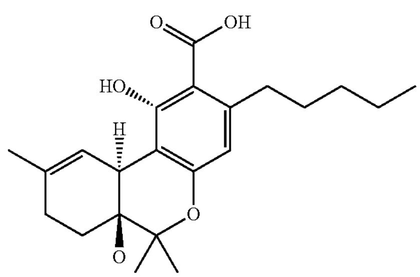 | 98523 (Δ9-Tetrahydrocannabinolic acid or THCA) | −7.17 | −10.89 |
| T4 | 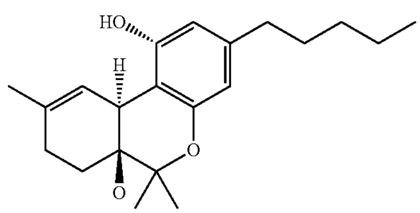 | 16078 (Donabinol or $\Delta^9$-THC) | −7.13 | −10.42 |
| T5 | 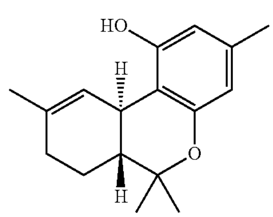 | 22805640 ($\Delta^1$-Tetrahydrocannabiorcol) | −7.11 | −9.88 |
| T6 | 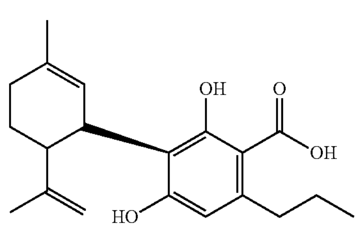 | 59444387 (Cannabidivarinic acid) | −7.10 | −10.39 |

TABLE 1-continued
| Groups | Chemical Structure | PubChem Ids (Compounds) | Binding energy (kcal/mol) VINA | Binding energy (kcal/mol) AUTODOCK |
|---|---|---|---|---|
| T7 | 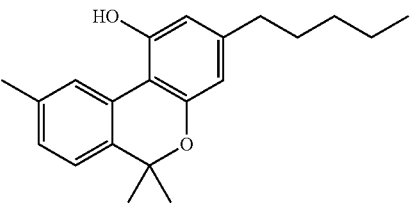 [SMILES: CCCCCc1cc(O)c2c(c1)OC(C)(C)c1ccc(C)cc1-2] | 2543 (Cannabinol) | −7.16 | −10.42 |
| T8 | 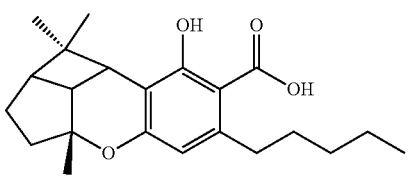 | 71437560 (Cannabicyclolic acid) | −7.07 | −10.63 |
| T9 | 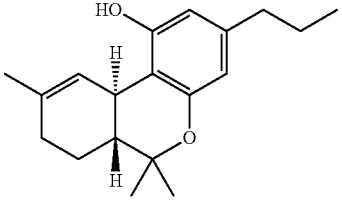 [SMILES: CCCc1cc(O)c2c(c1)OC(C)(C)[C@@H]1CCC(C)=C[C@@H]21] | 93147 (Tetrahydrocannabivarin) | −7.06 | −10.09 |
| T10 | 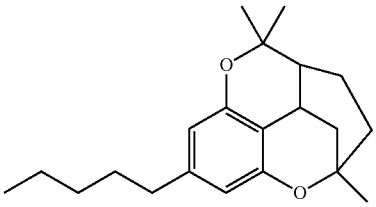 [SMILES: CCCCCc1cc2c3c(c1)OC(C)(C)C1CCC(C)(CC31)O2] | 59444393 (Cannabicitran) | −6.85 | −9.10 |
| T11 | 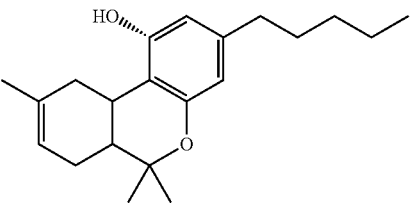 | 2977 (Δ$^8$-THC) | −6.82 | −9.25 |
| T12 | 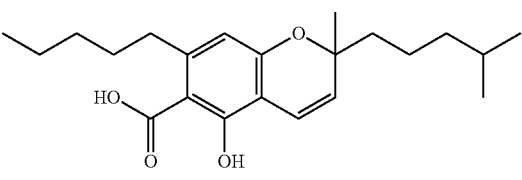 [SMILES: CCCCCc1cc2c(c(O)c1C(=O)O)C=CC(C)(CCCC(C)C)O2] | 3084339 (Cannabichromenic acid) | −6.82 | −9.90 |
| T13 | 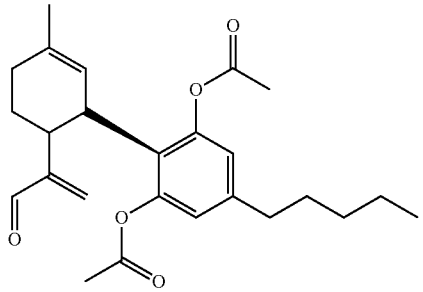 | 3044489 (Cannabidiol-aldehyde diacetate) | −6.78 | −10.32 |

TABLE 1-continued

| Groups | Chemical Structure | PubChem Ids (Compounds) | Binding energy (kcal/mol) VINA | Binding energy (kcal/mol) AUTODOCK |
|---|---|---|---|---|
| T14 | 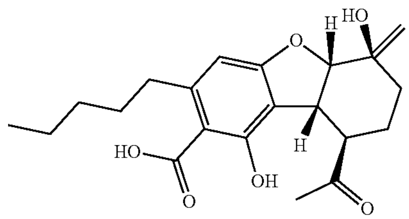 | 59444405 (Cannabielsoic acid A) | −6.75 | −9.85 |
| T15 | 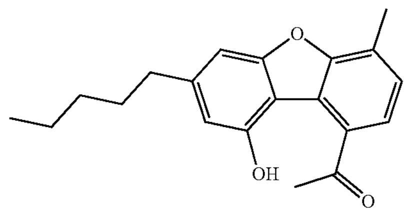 [SMILES: CCCCCc1cc(O)c2c(c1)oc1c(C)ccc(C(C)=O)c12] | 59444381 (Dehydrocannabifuran) | −6.75 | −9.51 |
| T16 | 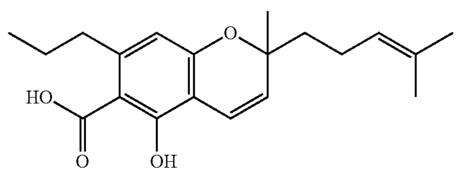 [SMILES: CCCc1cc2c(c(O)c1C(=O)O)C=CC(C)(CCC=C(C)C)O2] | 11110322 (Cannabichromevarinic acid) | −6.72 | −9.51 |
| T17 | 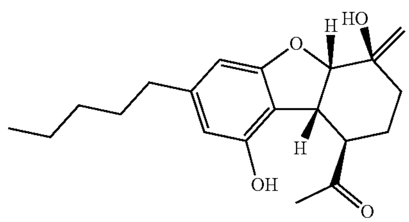 | 162113 (Cannabielsoin) | −6.60 | −9.45 |
| T18 | 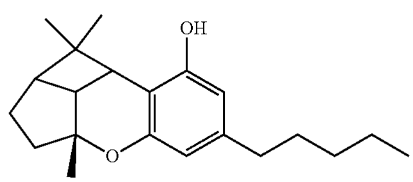 [SMILES: CCCCCc1cc(O)c2c(c1)O[C@]1(C)CCC3C1C2C3(C)C] | 30607 (Cannabipinol) | −6.58 | −10.35 |
| T19 | 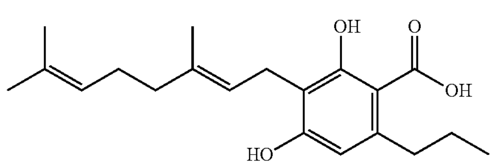 [SMILES: CCCc1cc(O)c(C/C=C(\C)CCC=C(C)C)c(O)c1C(=O)O] | 59444383 (Cannabigerovarinic acid) | −6.48 | −9.23 |
| T20 | 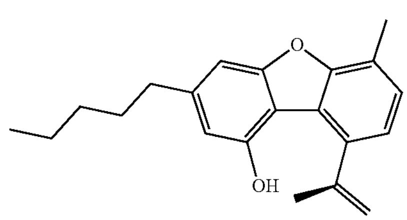 | 9966466 (Cannabifuran) | −6.43 | −9.89 |

TABLE 1-continued
| Groups | Chemical Structure | PubChem Ids (Compounds) | Binding energy (kcal/mol) VINA | Binding energy (kcal/mol) AUTODOCK |
|---|---|---|---|---|
| T21 | 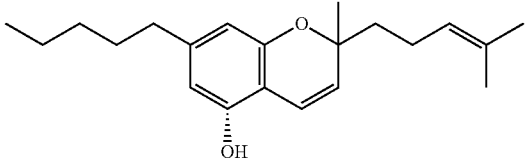 | 30219 (Cannabichrome) | −6.41 | −8.92 |
| T22 | 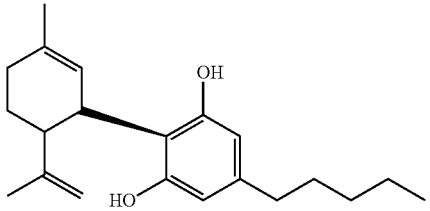 | 644019 (Cannabidiol) | −6.43 | −10.53 |
| T23 | 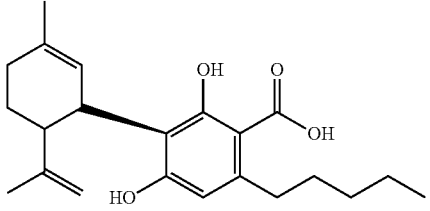 | 160570 (Cannabidiolic acid) | −6.39 | −10.44 |
| T24 | 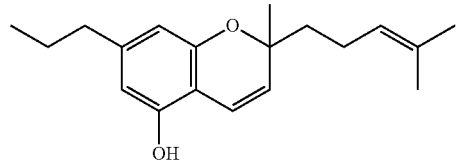 [SMILES: CCCc1cc(O)c2c(c1)OC(C)(CCC=C(C)C)C=C2] | 6451726 (Cannabivarichromene) | −6.39 | −8.84 |
| T25 | 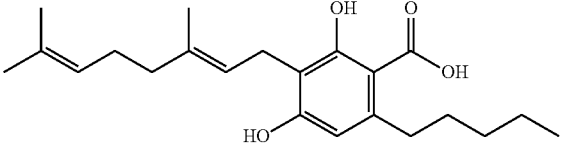 [SMILES: CCCCCc1cc(O)c(C/C=C(\C)CCC=C(C)C)c(O)c1C(=O)O] | 6449999 (Cannabigerolic acid) | −6.31 | −9.29 |
| T26 | 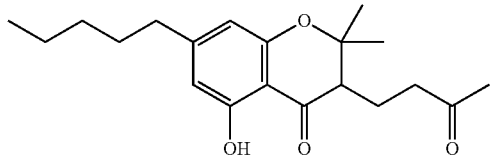 [SMILES: CCCCCc1cc(O)c2c(c1)OC(C)(C)C(CCC(C)=O)C2=O] | 186690 (Cannabichromanone) | −6.27 | −8.96 |
| T27 | 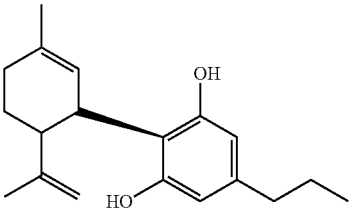 | 11601669 (Cannabidivarin) | −6.27 | −9.43 |

TABLE 1-continued

| Groups | Chemical Structure | PubChem Ids (Compounds) | Binding energy (kcal/mol) VINA | Binding energy (kcal/mol) AUTODOCK |
|---|---|---|---|---|
| T28 | 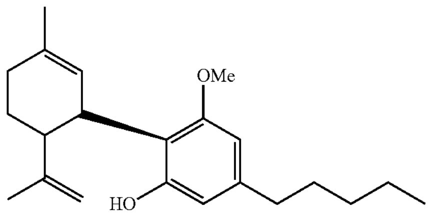 | 164905 (Cannabidiol-3-monomethyl ether) | −6.25 | −10.06 |
| T29 | 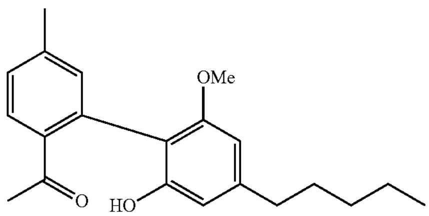 [SMILES: CCCCCc1cc(O)c(-c2cc(C)ccc2C(C)=O)c(OC)c1] | 11551346 (Cannabidinodiol) | −6.07 | −8.95 |
| T30 | 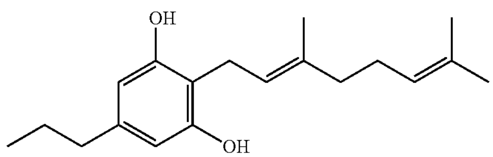 [SMILES: CCCc1cc(O)c(C/C=C(\C)CCC=C(C)C)c(O)c1] | 59444407 (Cannabigerovarin) | −5.94 | −8.40 |
| T31 | 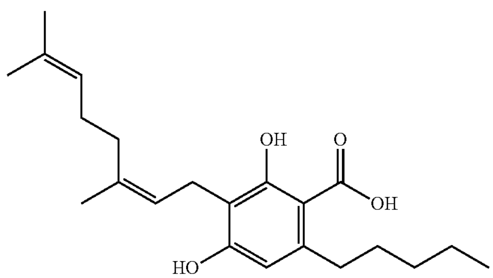 [SMILES: CCCCCc1cc(O)c(C/C=C(/C)CCC=C(C)C)c(O)c1C(=O)O] | 9998639 (Cannabinerolic acid) | −5.87 | −10.10 |
| T32 | 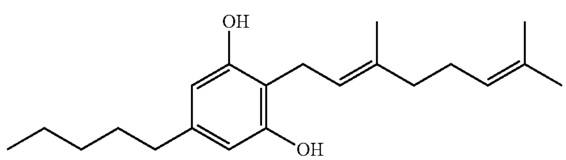 [SMILES: CCCCCc1cc(O)c(C/C=C(\C)CCC=C(C)C)c(O)c1] | 5315659 (Cannabigerol) | −5.67 | −8.70 |

The active site of SARS-CoV-2 $M^{Pro}$ was identified using the CASTp server by randomized 25 runs. As a result, it was determined that domain-I of SARS-CoV-2 $M^{Pro}$ was allocated as an active pocket for CBD docking (FIG. 1). This was consistent with the results of α-ketoamide 13b.

All molecules belonging to cannabinoids (CBDs) were shown to bind to SARS-CoV-2 $M^{Pro}$ with the binding energies of −5.67 to −7.62 kcal/mol (VINA) (Table 1). Redocking of 32 cannabinoids (CBDs) was performed using AUTODOCK, and all 32 CBDs had the binding energies between −8.40 kcal/mol and −10.89 kcal/mol (Table 1). In addition, based on molecular docking stability and interactions with SARS-CoV-2 $M^{Pro}$ residues, it was determined that $Δ^9$-THCA, $Δ^9$-THC, CBN, CBD, and CBDA of the 32 cannabinoids (CBDs) exhibited stable docking and binding to SARS-CoV-2 $M^{Pro}$ (FIGS. 3 and 4).

$Δ^9$-THCA, CBN, and CBDA had the binding energies of −10.89, −10.42, and −10.44 kcal/mol by AUTODOCK, respectively. $Δ^9$-THC and CBD had the binding energies of −10.42 and −10.53 kcal/mol, respectively. The positive control, α-ketoamide 13b, had the binding energy of −9.50 kcal/mol.

Figure 3:
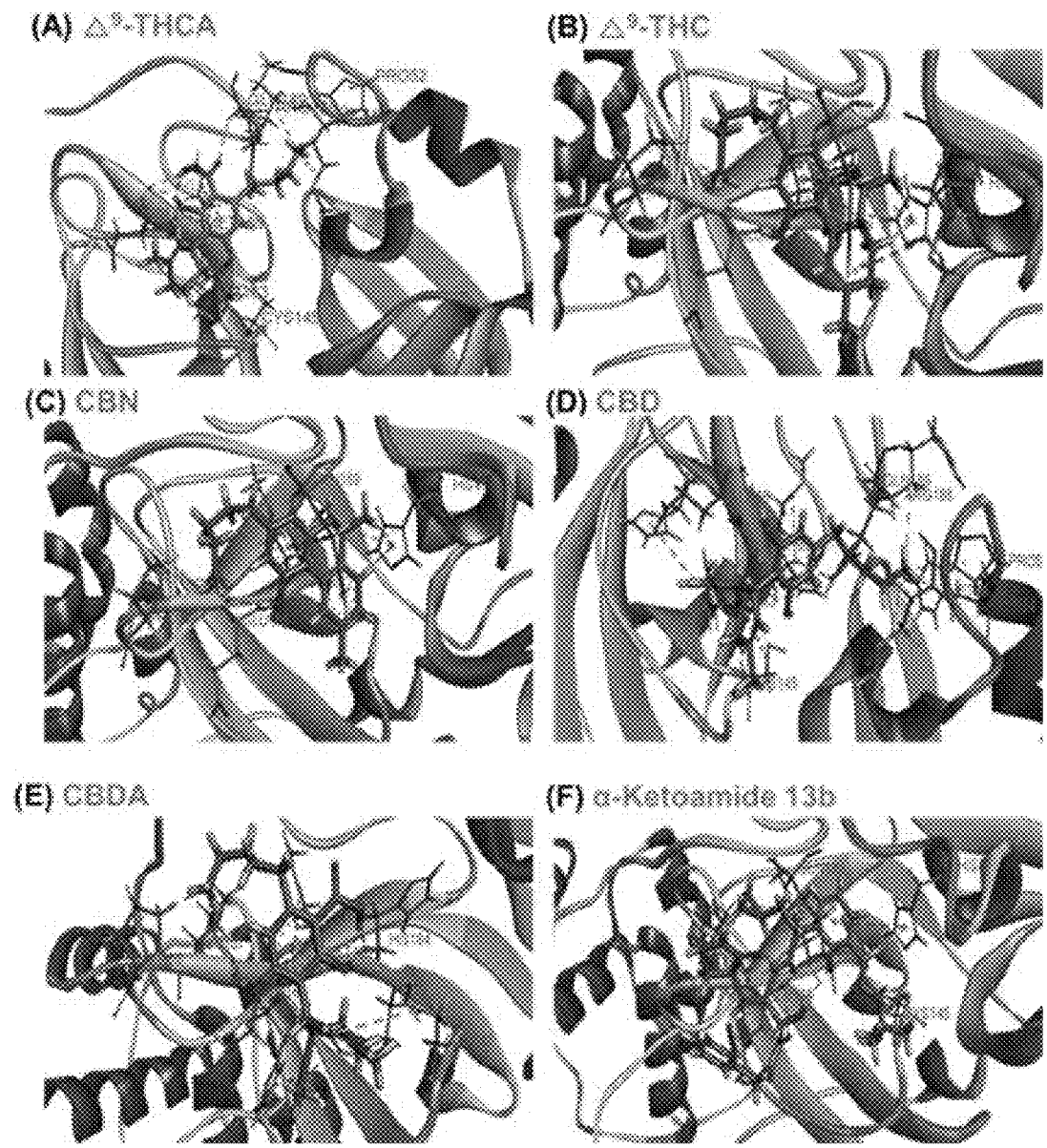
FIG. 3 shows ligand-protein interactions of SARS-CoV-2 $M^{Pro}$ with $\Delta^9$-THCA, $\Delta^9$-THC, CBN, CBD, CBDA and α-ketoamide 13b (positive control) in 3D form, where each green dotted line indicates hydrogen bonding between residues between SARS-CoV-2 $M^{Pro}$ and the ligand.
Figure 4:
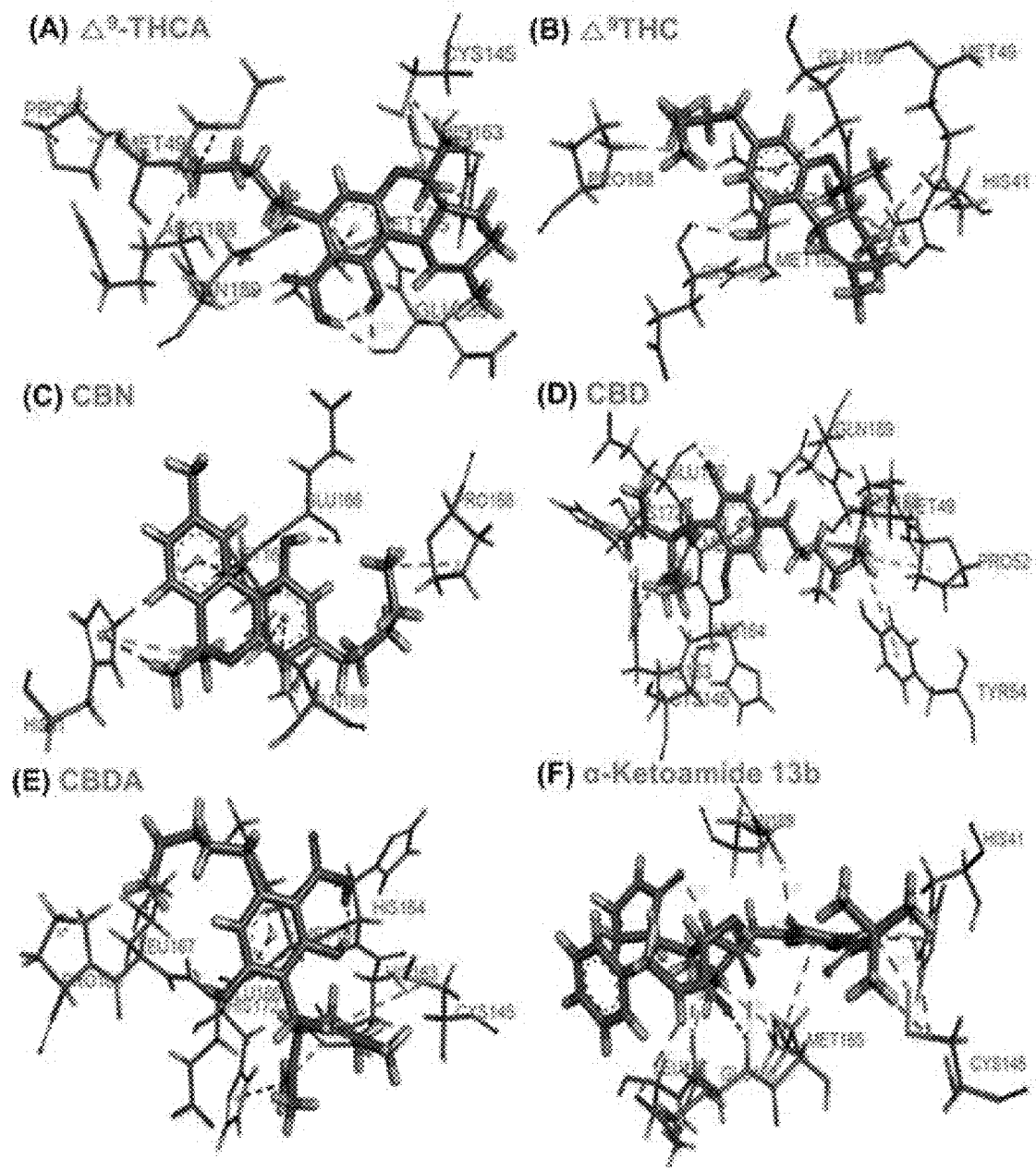
FIG. 4 shows ligand-protein interactions of SARS-CoV-2 $M^{Pro}$ with $\Delta^9$-THCA, $\Delta^9$-THC, CBN, CBD, CBDA, and α-ketoamide 13b (positive control).

The interaction between $Δ^9$-THC and SARS-CoV-2 $M^{Pro}$ involves one hydrogen bond and ten π-π bond interacting residues (FIG. 3).

The CBD-SARS-CoV-2 $M^{Pro}$ complex showed two hydrogen bonds and ten π-π interactions with various amino acid residues. Further, $Δ^9$-THCA, CBN, and CBDA showed 2, 1, and 3 hydrogen bonds and 10, 8, and 8 π-π interactions with amino acid residues, respectively.

Importantly, five molecules ($Δ^9$-THCA, $Δ^9$-THC, CBN, CBD, and CBDA) bound to SARS-CoV-2 $M^{Pro}$ and the positive control, α-ketoamide 13b interact with GLN189, MET165, and GLU166 residues of SARS-CoV-2 $M^{Pro}$. This suggests that the interactions with these residues are required to inhibit SARS-CoV-2 $M^{Pro}$. In particular, this means that hydrogen bonding, π-π bonding, and other intramolecular interactions between amino acid residues of SARS-CoV-2 M$^{Pro}$ and five selected cannabinoid (CBDs) molecules have better three-dimensional structural stability compared with other cannabinoid (CBDs) molecules.

In addition, binding of the five cannabinoids (CBDs), A9-THCA, Δ$^9$-THC, CBN, CBD, and CBDA, using the binding pocket of SARS-CoV-2 M$^{Pro}$ resulted in higher docking scores than the five reference compounds, favipiravir, bondducellpin D, ribavirin, raltegravir, and α-ketoamide (Table 1 and Table 2).

Table 2 below shows the molecular binding affinities of SARS-CoV-2 M$^{Pro}$ and CBD, where bold font indicates common amino acid residues. Δ$^9$-THCA, Δ$^9$-THC, CBN, CBD, and CBDA are cannabinoids (CBDs) compounds tested as described above, and PC stands for a positive control.

TABLE 2

| Chemical structure | Compounds (PubChem Id) | Binding energy (kcal/mol) VINA | Binding energy (kcal/mol) AUTODOCK | interacting amino acid residues | Bonds |
|---|---|---|---|---|---|
| 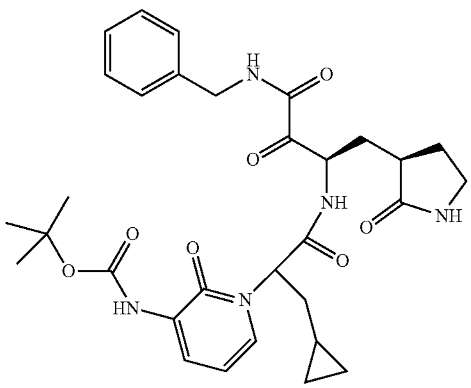 | α-ketoamide 13b (Zhang et al., 2020b) | −7.11 | −9.50 | HIS41, CYS145, MET165, GLU166, LEU167, GLN189. | 6 π-π, 6 H |
| | Δ$^9$-Tetrahydrocannabinolic acid or Δ$^9$-THCA (98523) | −7.17 | −10.89 | MET49, PRO52, CYS145, HIS163, MET165, GLU166, ARG188, GLN189. | 10 π-π, 2 H |
| | Δ$^9$-Tetrahydrocannabinol or Δ$^9$-THC (16078) | −7.13 | −10.42 | HIS41, MET49, MET165, GLU166, PRO168, GLN189. | 10 π-π, 1 H |
| 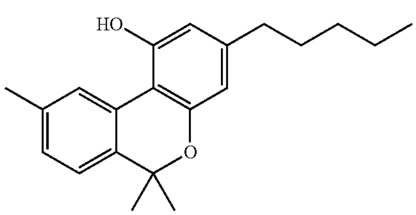 [SMILES: CCCCCc1cc(O)c2c(c1)OC(C)(C)c1ccc(C)cc1-2] | Cannabinol or CBN (2543) | −7.16 | −10.42 | HIS41, MET165, GLU166, PRO168, GLN189. | 8 π-π, 1 H |
| 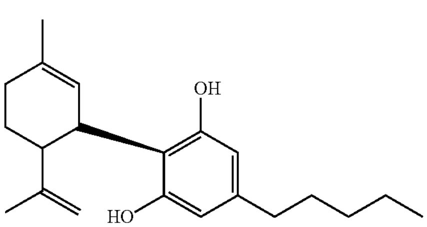 | Cannabidiol or CBD (644019) | −6.43 | −10.53 | MET49, PRO52, TYP54, CYS145, HIS163, HIS164, MET165, GLU166, HIS172, ARG188, GLN189. | 10 π-π, 2 H |

TABLE 2-continued

| Chemical structure | Compounds (PubChem Id) | Binding energy (kcal/mol) VINA | Binding energy (kcal/mol) AUTODOCK | interacting amino acid residues | Bonds |
|---|---|---|---|---|---|
| 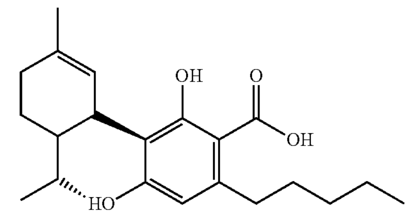 | Cannabidiolic acid or CBDA (160570) | −6.39 | −10.44 | CYS145, HIS163, HIS164, MET165, GLU166, LEU167, PRO168, HIS172 | 8 π-π, 3 H |

<Example 2> Absorption, Distribution, Metabolism, and Excretion Profiles of Cannabinoids (CBDs)

For energy-optimized cannabinoid (CBDs) molecular selection, Schrodinger software was used to analyze absorption, distribution, metabolism, and excretion (ADME) profiles. All cannabinoids (CBDs) showed acceptable molecular weight, Lipinski's violation, n-OHNH donors, n-OH acceptors, and n-ROTB according to Lipinski's rule (Table 3), and it was determined that these cannabinoids (CBDs) had the potential to exhibit excellent absorption profiles and pharmacological effects. Table 3 below shows the pharmacokinetic parameters indicating excellent oral bioavailability and protein binding parameters of cannabinoids (CBDs).

TABLE 3

| Compounds | % ABS | QPPCaco | n-ROTB | MW | Volume Rule | n-OHNH donors | n-OH acceptors | Lipinski's violation | QPlogPo |
|---|---|---|---|---|---|---|---|---|---|
|  | >80% is high <25% is poor | <25 poor >500 great | 0-15 | <500 | 500.0- to 2000.0 | <5 | <10 | ≤1 | −2.0 to 6 |
| T1 | 100 | 1404.14 | 7 | 346.47 | 1182.66 | 3 | 3.95 | 0 | 4.11 |
| T2 | 89 | 229.31 | 6 | 354.45 | 1188.49 | 1 | 2.5 | 1 | 5.60 |
| T3 | 90.33 | 250.26 | 6 | 358.48 | 1213.24 | 1 | 2.5 | 1 | 5.71 |
| T4 | 100 | 4339.75 | 5 | 314.47 | 1151.47 | 1 | 1.5 | 1 | 5.72 |
| T5 | 100 | 4336.67 | 1 | 258.36 | 909.83 | 1 | 1.5 | 0 | 4.18 |
| T6 | 93.66 | 155.82 | 6 | 330.42 | 1108.94 | 2 | 2.5 | 0 | 4.69 |
| T7 | 100 | 4302.23 | 5 | 310.44 | 1123.06 | 1 | 1.5 | 1 | 5.61 |
| T8 | 90.72 | 295.91 | 6 | 358.48 | 1183.00 | 1 | 2.5 | 1 | 5.55 |
| T9 | 100 | 4339.69 | 3 | 286.41 | 1029.85 | 1 | 1.5 | 0 | 4.94 |
| T10 | 100 | 9906.04 | 4 | 314.47 | 1112.14 | 0 | 1.5 | 1 | 5.03 |
| T11 | 100 | 2483.30 | 7 | 314.50 | 1375.85 | 0 | 7 | 0 | 4.49 |
| T12 | 90.42 | 191.09 | 9 | 358.48 | 1276.22 | 1 | 2.5 | 1 | 6.08 |
| T13 | 100 | 1159.65 | 8 | 412.53 | 1392.62 | 0 | 7 | 0 | 4.39 |
| T14 | 81.74 | 137.94 | 8 | 374.48 | 1218.09 | 2 | 3.25 | 1 | 5.03 |
| T15 | 100 | 5986.17 | 6 | 308.42 | 1103.79 | 1 | 1.25 | 1 | 5.72 |
| T16 | 85.82 | 190.76 | 7 | 330.42 | 1134.09 | 1 | 2.5 | 1 | 5.30 |
| T17 | 100 | 1817.87 | 7 | 330.47 | 1146.73 | 2 | 2.25 | 0 | 4.87 |
| T18 | 100 | 4558.09 | 5 | 314.47 | 1129.84 | 1 | 1.5 | 1 | 5.57 |
| T19 | 80.29 | 109.52 | 10 | 332.44 | 1192.93 | 2 | 2.5 | 1 | 5.09 |
| T20 | 100 | 5640.48 | 6 | 310.44 | 1117.73 | 1 | 1.25 | 1 | 5.76 |
| T21 | 100 | 3567.62 | 8 | 314.47 | 1210.28 | 1 | 1.5 | 1 | 6.09 |
| T22 | 100 | 2598.78 | 7 | 314.47 | 1168.40 | 2 | 1.5 | 1 | 5.43 |
| T23 | 85.23 | 156.13 | 8 | 358.48 | 1230.77 | 2 | 2.5 | 1 | 5.46 |
| T24 | 100 | 3567.63 | 6 | 286.41 | 1088.07 | 1 | 1.5 | 1 | 5.30 |
| T25 | 85.18 | 110.50 | 12 | 360.49 | 1321.38 | 2 | 2.5 | 1 | 5.91 |
| T26 | 100 | 749.87 | 8 | 332.44 | 1191.46 | 0 | 4.5 | 0 | 4.14 |
| T27 | 100 | 2580.18 | 5 | 286.41 | 1038.28 | 2 | 1.5 | 0 | 4.61 |
| T28 | 100 | 5301.80 | 7 | 328.49 | 1227.42 | 1 | 1.5 | 1 | 6.27 |

% ABS, percentage of absorption;
QPPCaco, predicted apparent Caco-2 cell permeability in nm/sec, production of binding to human serum albumin;
n-ROTB, roratable bonds;
MW, moleculer volume;
Volume, Total solvent-accessible volume in cubic angstroms using a probe of 1.4 Å radius;
n-OHN donors, number of hydrogen bond donors;
n-ON, number of hydrogen bond acceptors;
QPlogPo/w, predicted octanol/water partition coefficient.

<Example 3> Confirmation of Stability of Cannabinoids (CBDs) Determined by Density Functional Theory (DFT)

Figure 5:
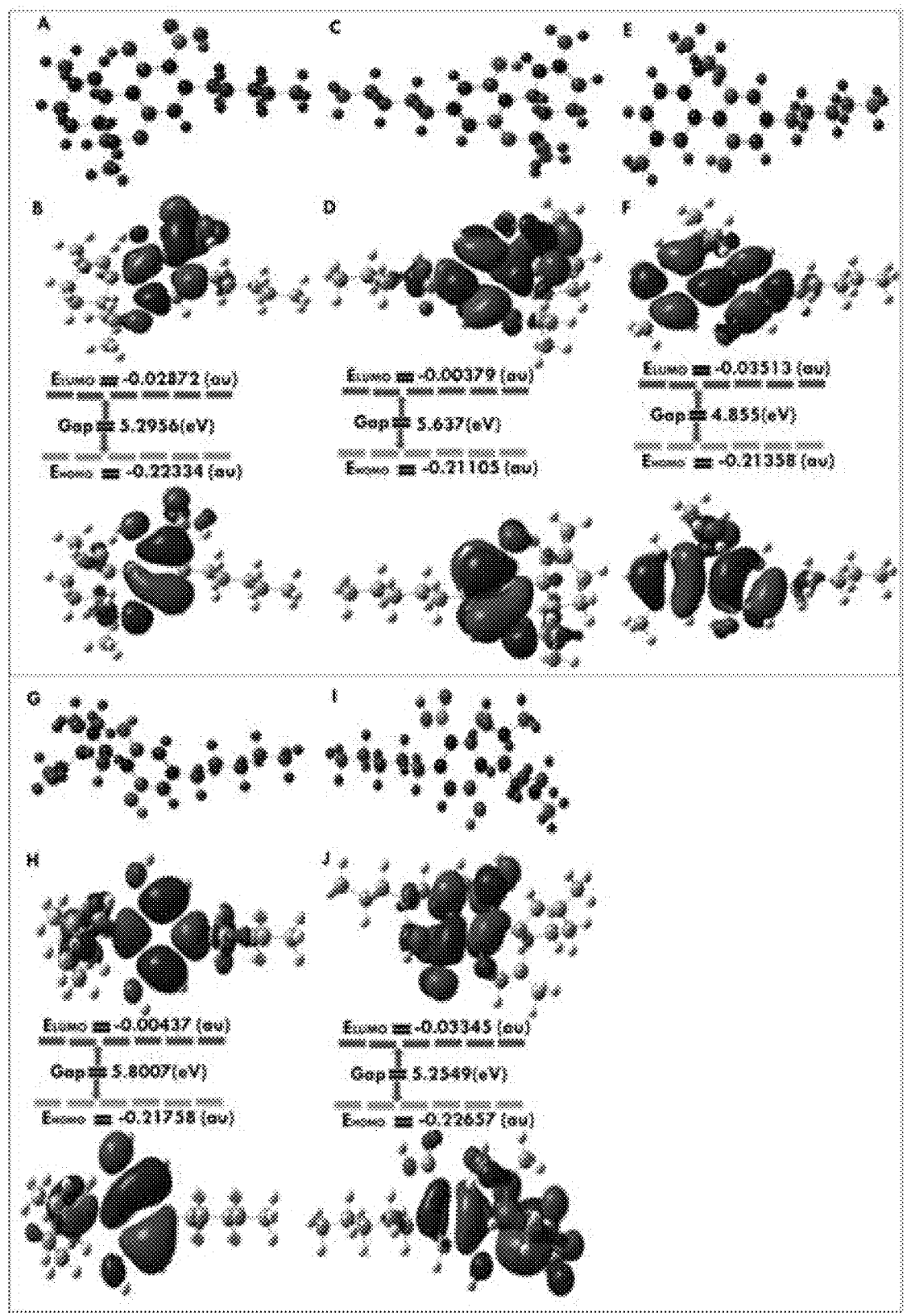
FIG. 5 shows the optimized molecular shapes with the charge and atomic number for A. $\Delta^9$-THCA, C. $\Delta^9$-THC, E. CBN, G. CBD, and I. CBD as frontier molecular orbitals, and B. Δ⁹-THCA, D. Δ⁹-THC, F. CBN, H. CBD, and J. CBDA show frontier molecular orbitals used to determine HOMO-LUMO.
Figure 6A:
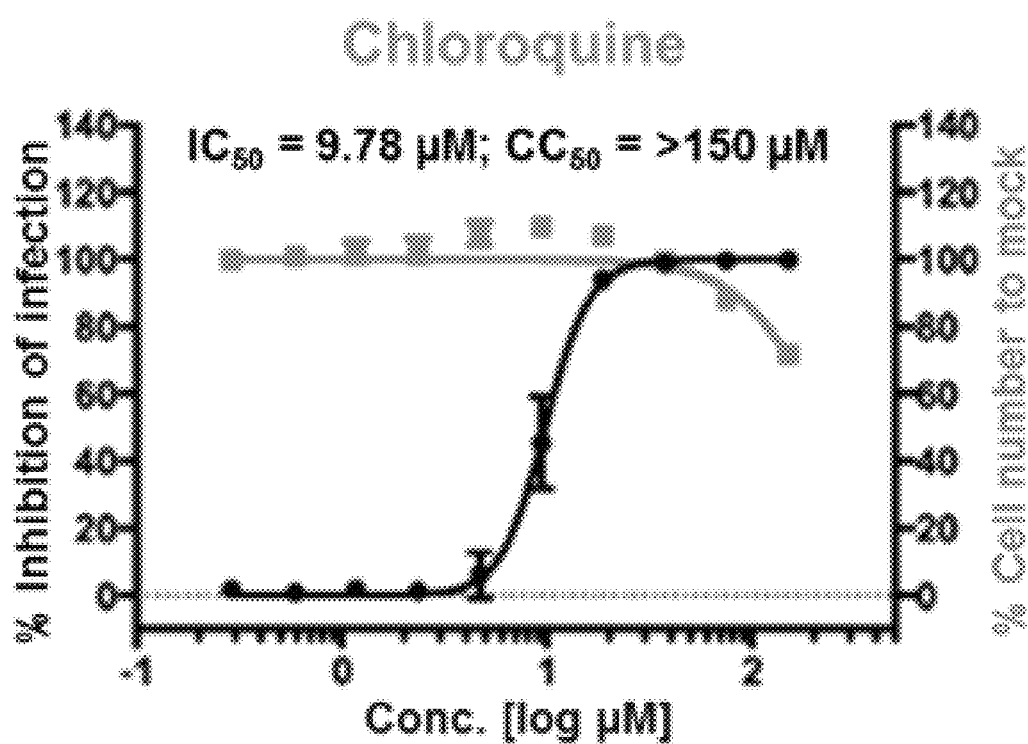
FIGS. 6A-6H show analysis results of dose-response curves for the control drugs, lopinavir, chloroquine, and remdesivir, and Δ⁹-THCA, Δ⁹-THC, CBN, CBD and CBDA, where the blue lines indicate SARS-CoV-2 infection inhibition (%), and the red lines indicate Vero cell viability (%) (mean±SD calculated from the results of duplicate experiments).
Figure 6B:
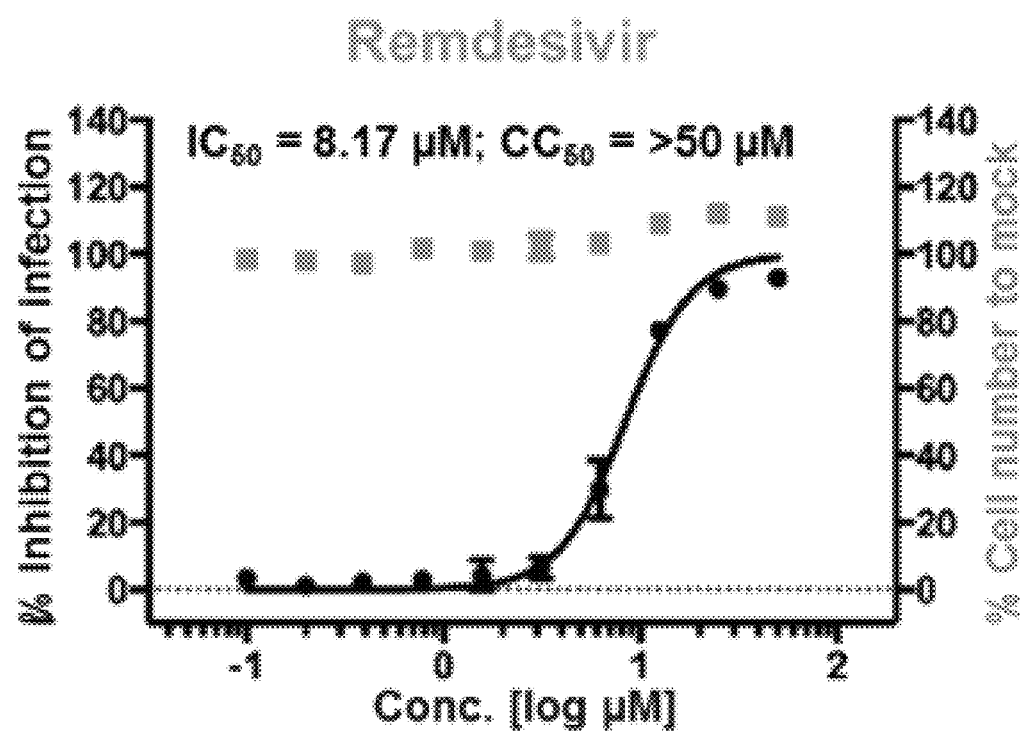
Figure 6C:
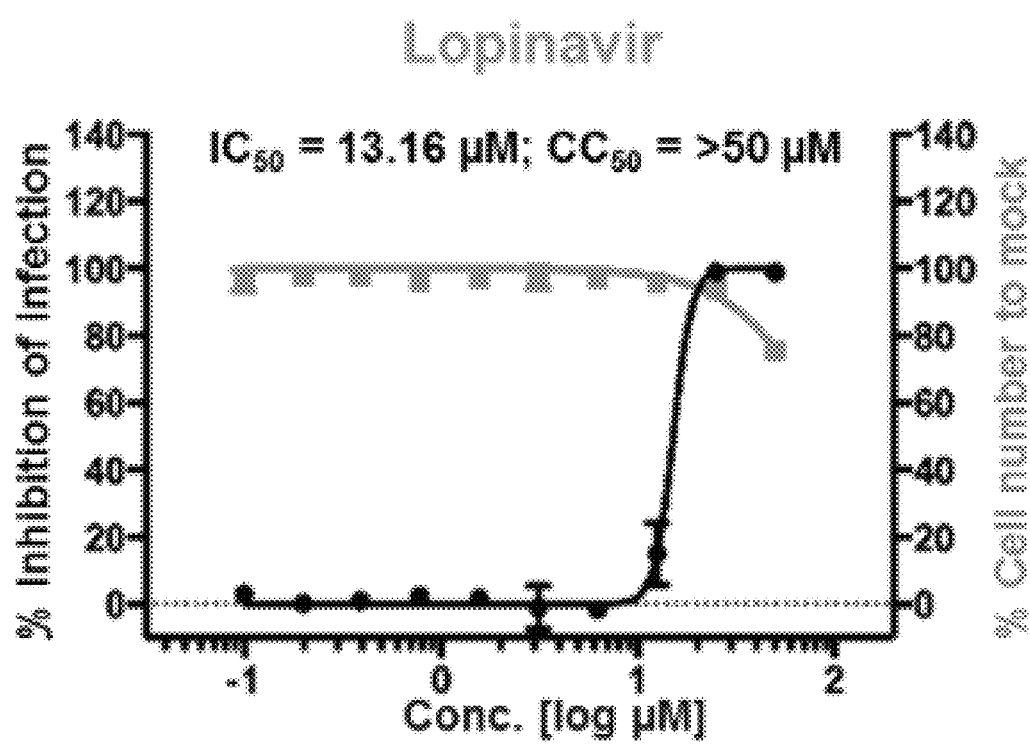
Figure 6D:
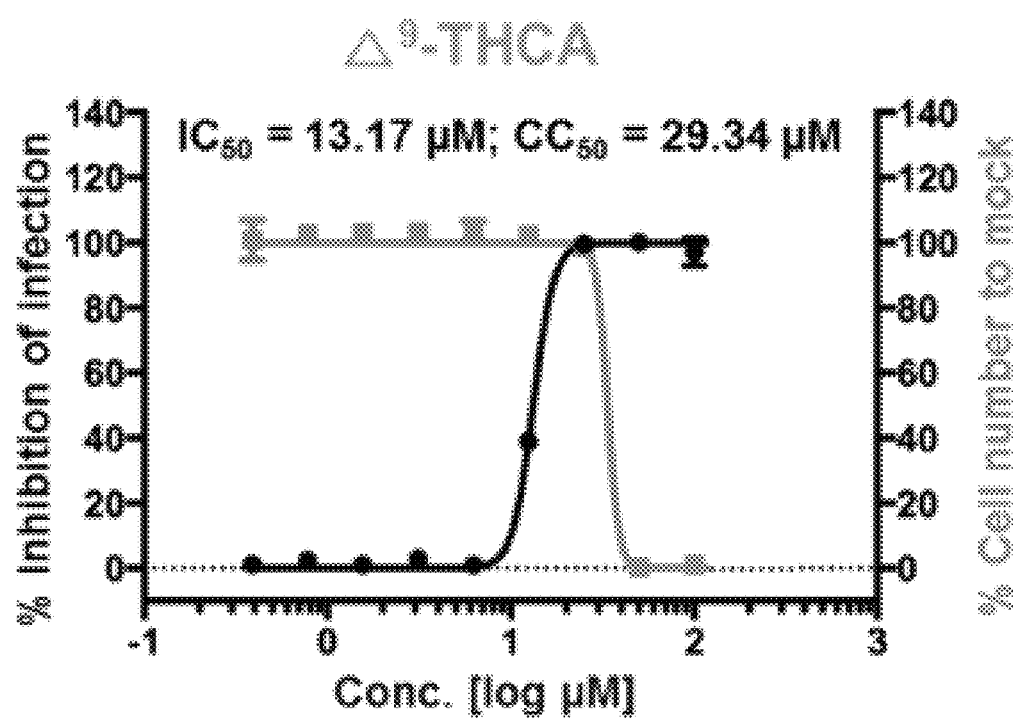
Figure 6E:
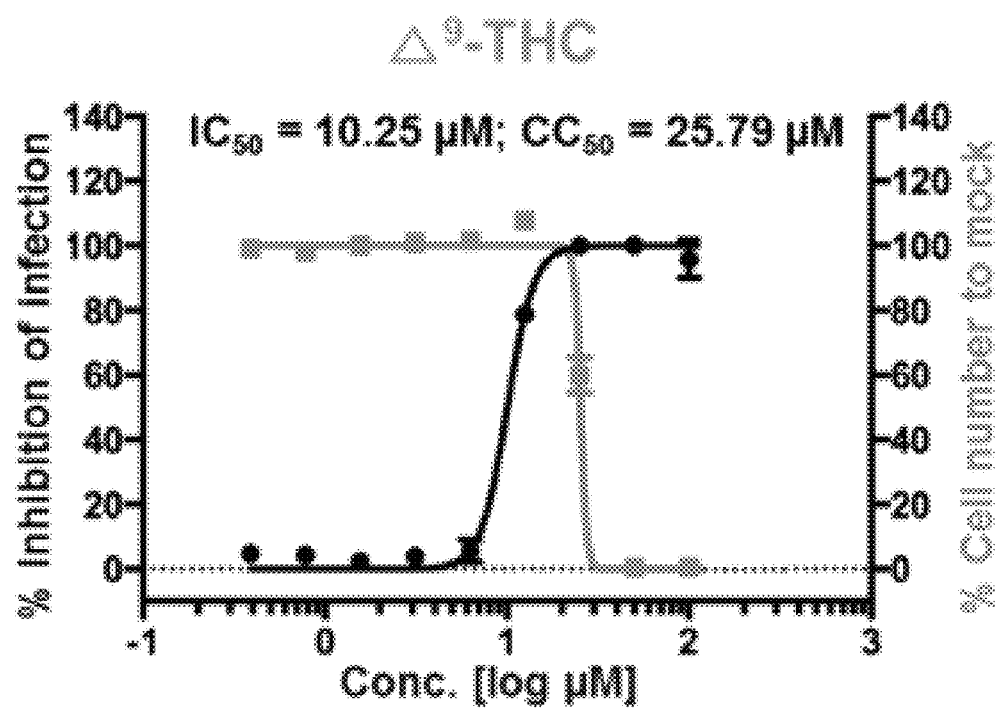
Figure 6F:
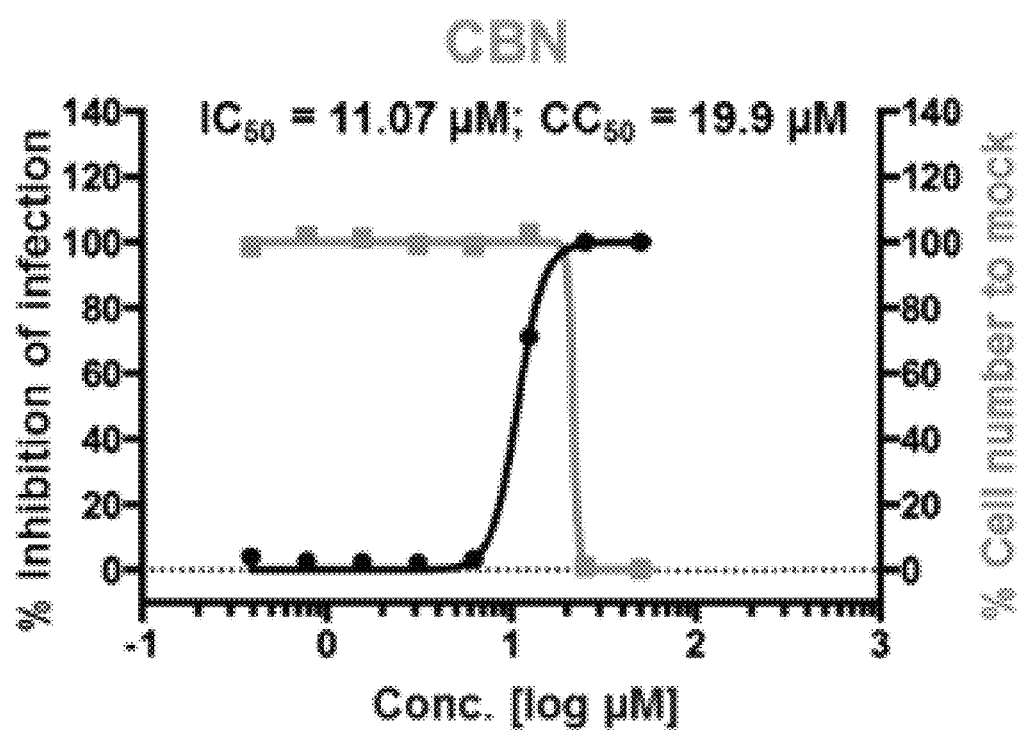
Figure 6G:
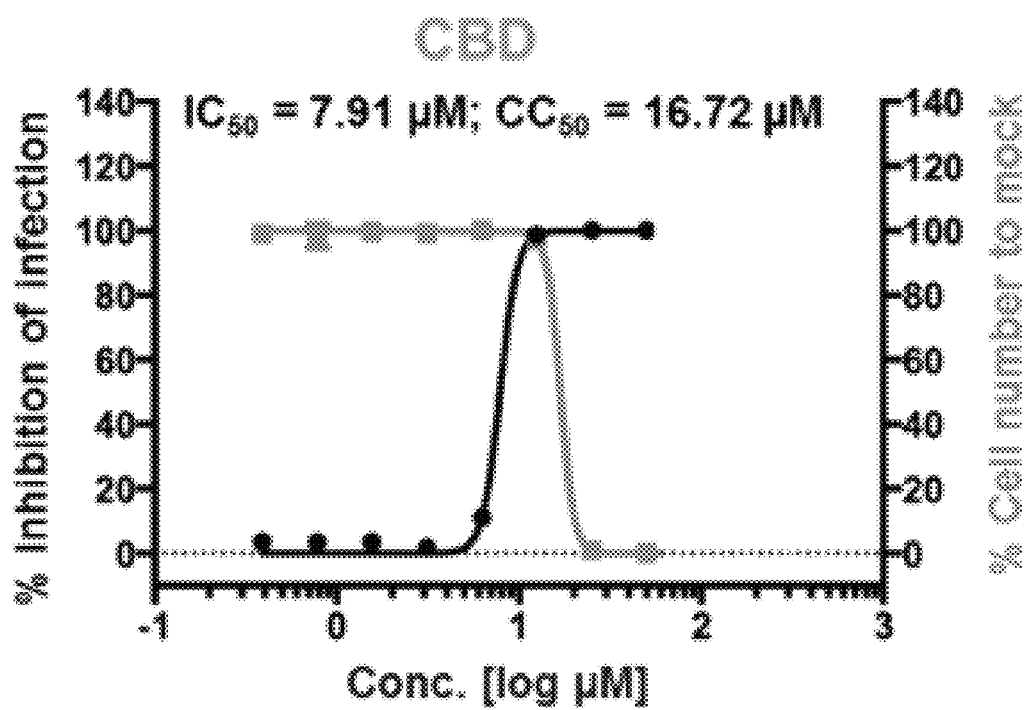
Figure 6H:
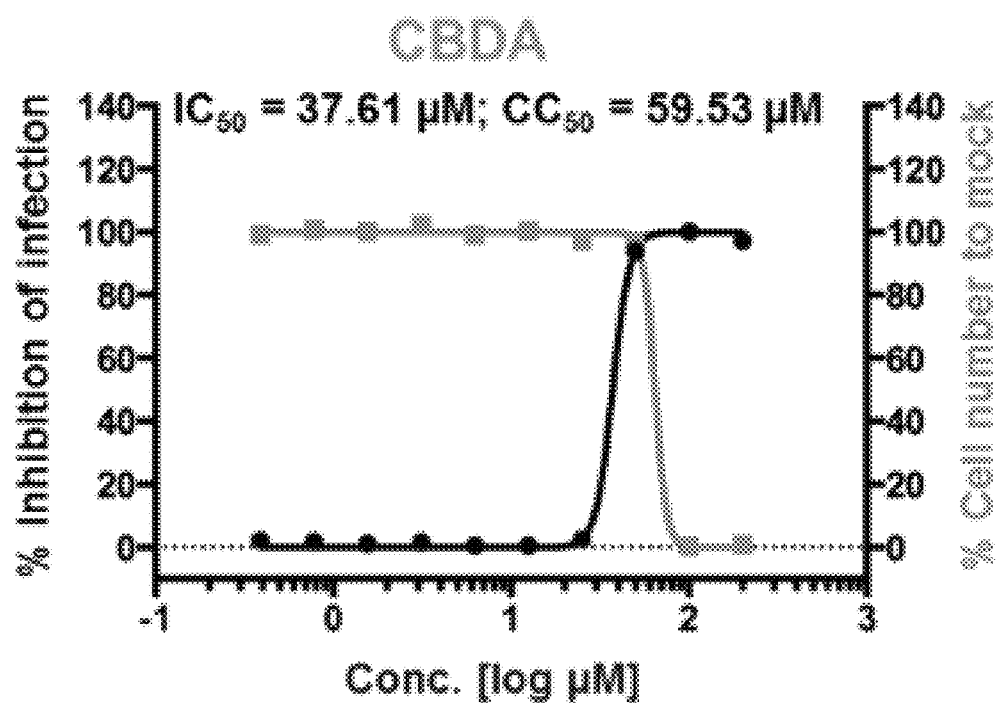
Figure 7A:
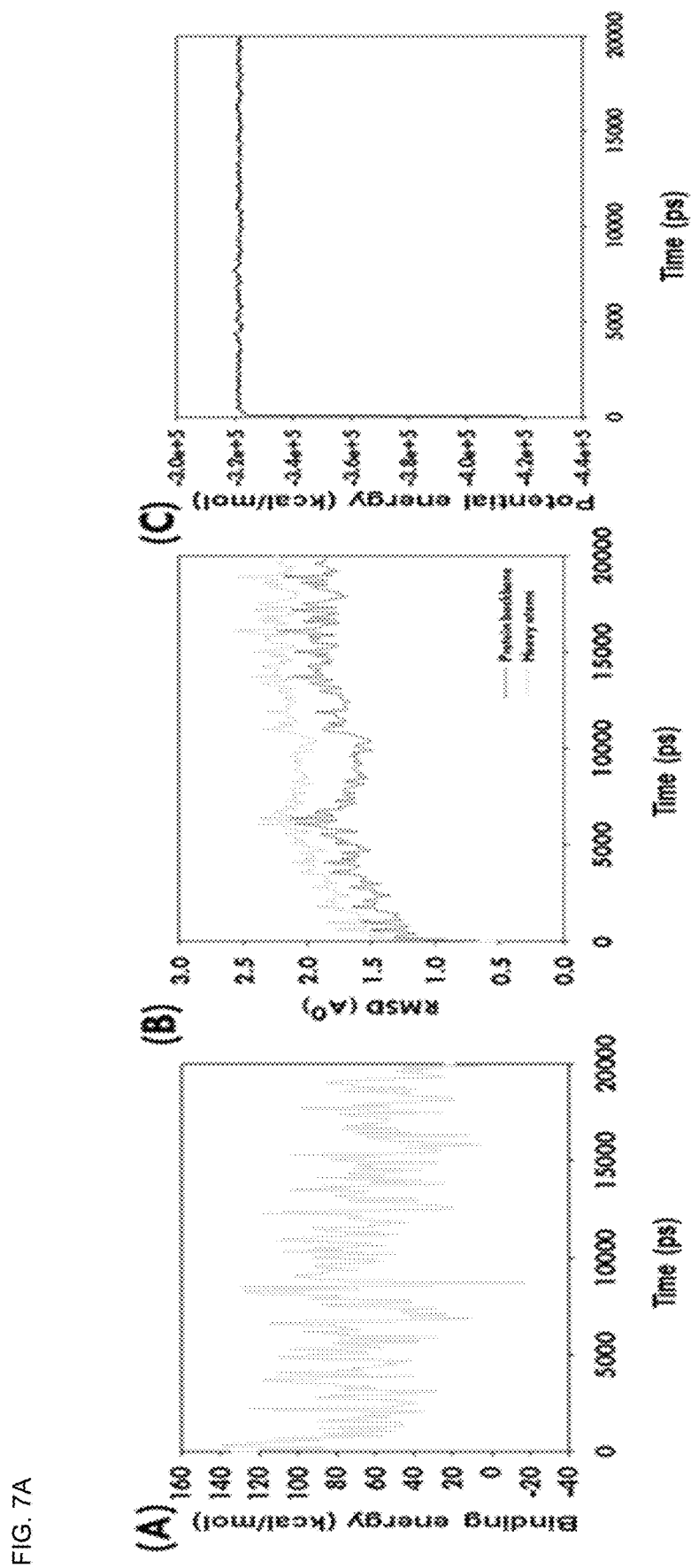
FIGS. 7A-7E show plots depicting interaction stability between cannabinoids (CBDs) and the SARS-CoV-2 $M^{Pro}$ complex in molecular docking (MD) simulations over time. More specifically, (A-C) depict the binding energy profile, RMSD, and potential energy of Δ⁹-THCA-SARS-CoV-2 $M^{Pro}$ complex, (D-F) depict the binding energy profile, RMSD, and potential energy of CBN-SARS-CoV-2 $M^{Pro}$ complex, (G-I) depict the binding energy profile, RMSD, and potential energy of the CBDA-SARS-CoV-2 $M^{Pro}$ complex, and (J-L) depict the binding energy profile, RMSD, and potential energy of the Δ⁹-THC-SARS-CoV-2 $M^{Pro}$ complex, and (M-O) depict the binding energy profile, RMSD, and potential energy of the CBD-SARS-CoV-2 $M^{Pro}$ complex.
Figure 7B:
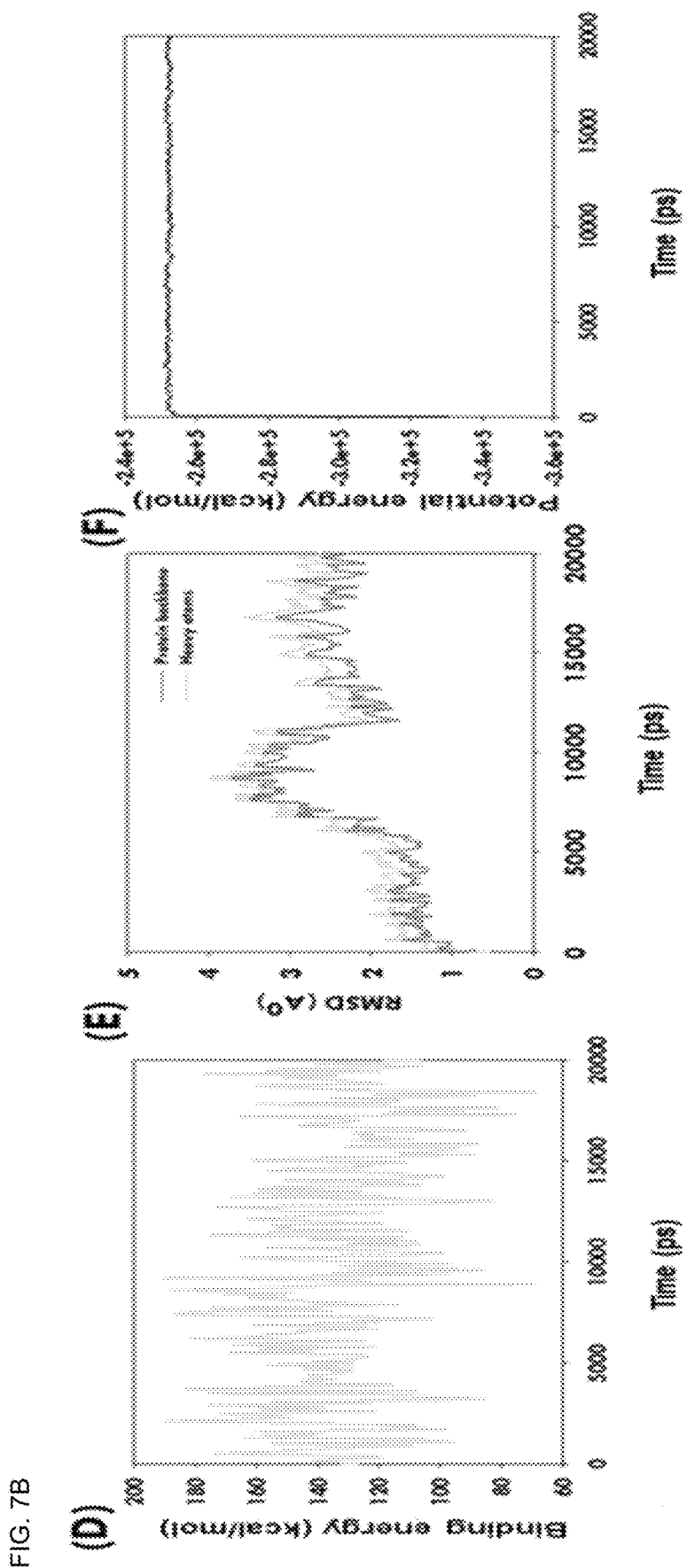
Figure 7C:
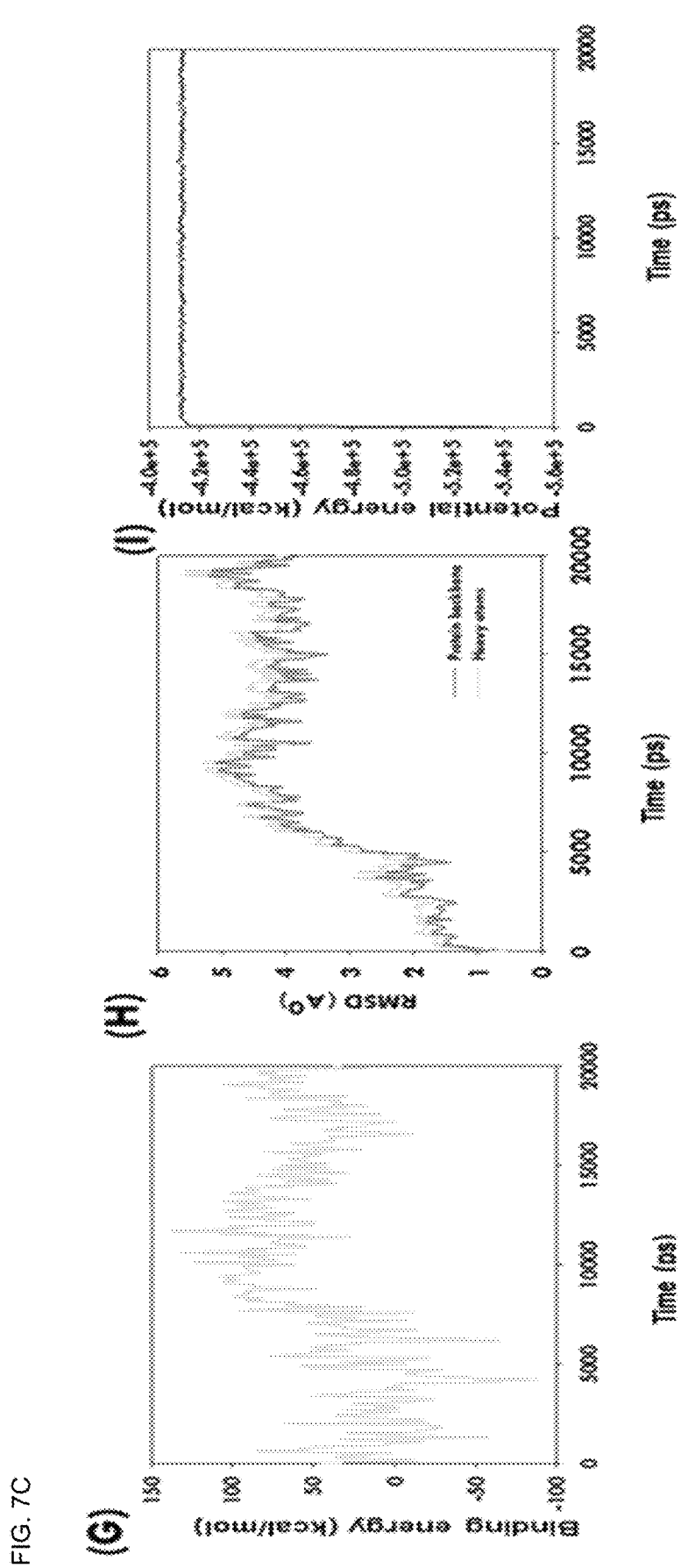
Figure 7D:
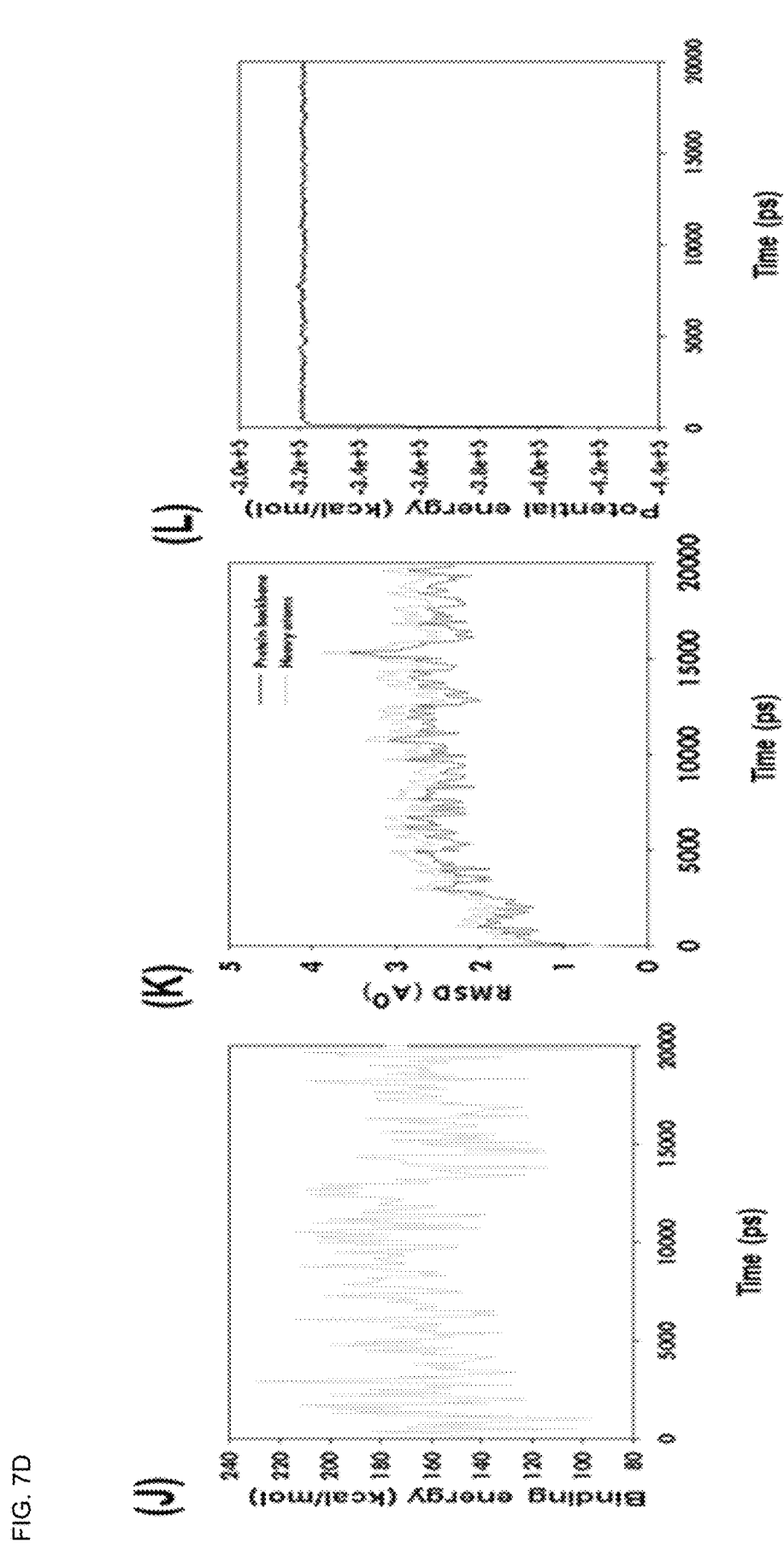
Figure 7E:
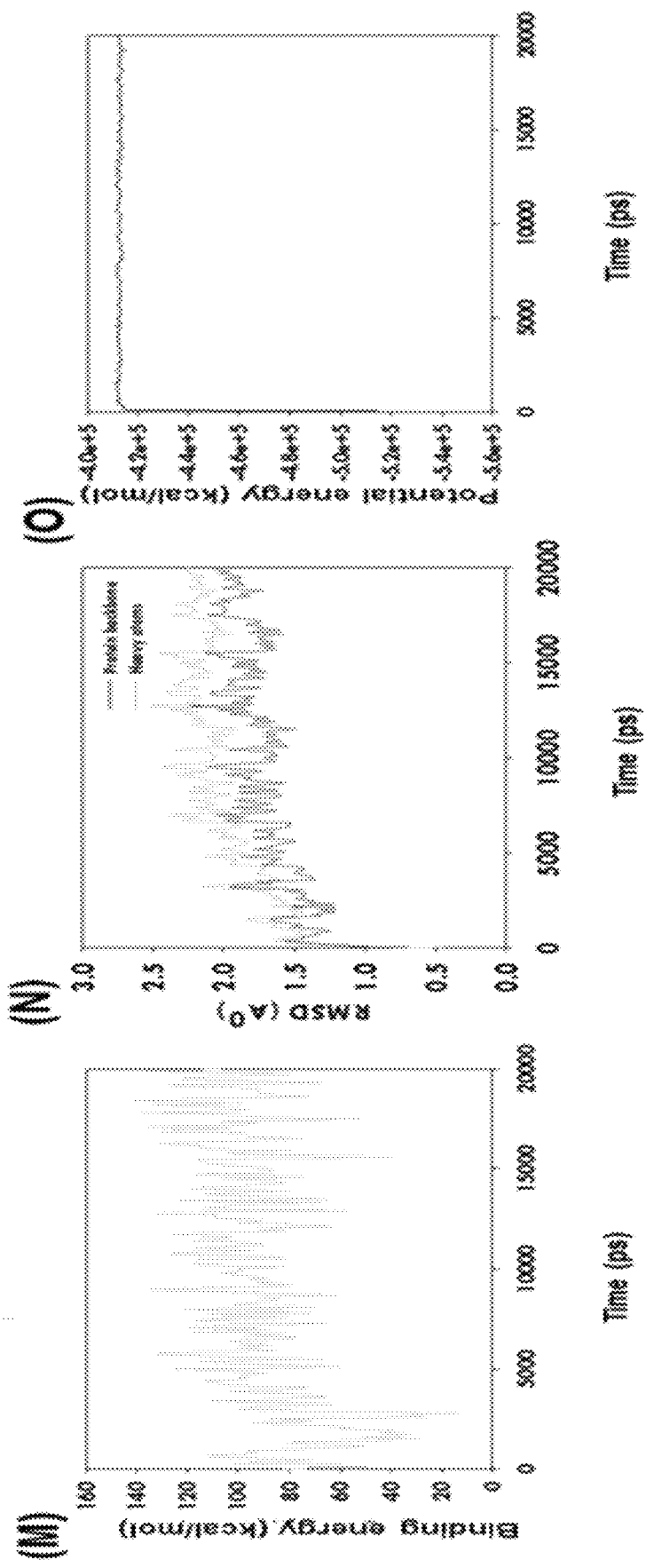

The HOMO versus LUMO energy gaps for five cannabinoids (CBDs) molecules were calculated using the density functional theory (DFT) and a Gaussian program package. The HOMO orbitals of $\Delta^9$-THC and CBD resided on 2,2-dimethylchroman-5-ol and methyl-1', 2', 3', 4'-tetrahydro-[1,1'-biphenyl]-2, 6-diolring motifs, respectively (FIG. 5).

The energy gap was found to be much higher in A9-THC and CBD than in CBDA. However, the LUMO of $\Delta^9$-THC and CBD resided on 3-propyl-6a, 7, 8, 10a-tetrahydro-6H-benzo[c]chromen-1-ol and [(S)-4, 5'-dimethyl-1', 2', 3', 4'-tetrahydro-[1, 1'-biphenyl]-2, 6-diol] motifs, respectively (FIG. 5).

The HOMO orbitals of $\Delta^9$-THCA, CBN, and CBDA located on chromene with a carboxylic acid group, a cyclic ring fused with chromene with an aliphatic side chain, and a dihydroxyl benzoic acid group, respectively.

It is already well known that a molecule with a small frontier energy orbital gap is highly chemically reactive, highly polar, and has low kinetic stability, and that a high HOMO-LUMO gap between frontier orbitals leads to high stability (Table 4). Table 4 shows density functional theory (DFT) calculations of cannabinoids (CBDs) for quantum chemical parameters.

TABLE 4

| Quantum chemical parameters (eV unit) | $\Delta^9$-THCA | $\Delta^9$-THC | CBN | CBD | CBDA |
|---|---|---|---|---|---|
| HOMO | −6.07 | −5.74 | −5.81 | −5.91 | −6.16 |
| LUMO | −0.78 | −0.10 | −0.95 | −0.11 | −0.91 |
| Energy gap (ΔE) | 5.29 | 5.63 | 4.85 | 5.80 | 5.25 |
| Chemical potential (p) | 3.42 | 2.92 | 3.38 | 3.01 | 3.53 |
| Global hardness (η) | 2.64 | 2.82 | 2.42 | 2.90 | 2.62 |
| Ionization potential (I) | 6.07 | 5.74 | 5.81 | 5.91 | 6.16 |
| Electrophilicity (ω) | 2.21 | 1.51 | 2.37 | 1.56 | 2.37 |

The compounds $\Delta^9$-THC and CBD had higher HOMO-LUMO energy gaps than $\Delta^9$-THCA, CBN, and CBDA, indicating that $\Delta^9$-THC and CBD were more stable. Chemical hardness (η) is defined as the resistance to distortion of the electron cloud during chemical processes, which indicates the stability of a compound. Interestingly, since the chemical hardness (η) values of $\Delta^9$-THC and CBD were higher than those of $\Delta^9$-THCA, CBN, and CBDA, $\Delta^9$-THC and CBD showed the best stability.

<Example 4> Evaluation of In Vitro Antiviral Effect of Cannabinoids (CBDs) on SARS-CoV-2

The purpose of this study was to evaluate the in vitro antiviral effect of cannabinoids (CBDs) on SARS-CoV-2. As previously confirmed, five molecules belonging to cannabinoids (CBDs), i.e. $\Delta^9$-THCA, $\Delta^9$-THC, CBN, CBD, and CBDA, were obtained by successful isolation and purification (Table 2 and FIGS. 2A-2F), and Vero cells were was used to evaluate antiviral activity in vitro.

Viral N protein and cell nuclei were observed by confocal microscopy using in-house Image Mining (IM) software, and dose-response curves (DRCs) were derived for the cannabinoid (CBDs) molecules (FIGS. 6A-6H). In this experiment, lopinavir, chloroquine, and remdesivir were used as standard drugs. $IC_{50}$ values were 9.78, 8.17, and 13.16 µM, respectively, which were consistent with the result of the previous study (Jeon, S., Ko, M., Lee, J., Choi, I., Byun, S Y, Park, S., Shum, D., and Kim, S. (2020). Identification of antiviral drug candidates against SARS-CoV-2 from FDA-approved drugs. Antimicrobial Agents and Chemotherapy).

Among the cannabinoids (CBDs) molecules, $\Delta^9$-THC and CBD showed potential antiviral activity against SARS-CoV-2 with $IC_{50}$ values of 10.25 and 7.91 µM, respectively, whereas $\Delta^9$-THCA, CBN, and CBDA showed moderate antiviral activity with $IC_{50}$ values of 13.17, 11.07, and 37.61 µM, respectively.

The most active compound CBD showed high inhibition of SARS-CoV-2 virus at the concentration of 12.50 µM (99.19%) and the Vero cell viability was 97.46% (FIGS. 6A-6H). In addition, it was found that the host cell viability decreased sharply at the concentration of 50 µM. Therefore, CBD at 12.50 µM can be considered safe to inhibit SARS-CoV-2 without inducing cytotoxicity in vitro.

On the other hand, there is a report that administering CBD at 0.3 mg/kg/day is effective for Crohn's disease. In humans, CBD has been tested over a wide dose range from <1 to 50 mg/kg/day (Costiniuk, C T, Saneei, Z., Routy, J.-P., Margolese, S., Mandarino, E., Singer, J., Lebouché, B., Cox, J., Szabo, J., and Brouillette, M.-J. (2019). Oral cannabinoids in people living with HIV on effective antiretroviral therapy: CTN PT028-study protocol for a pilot randomized trial to assess safety, tolerability and effect on immune activation. BMJ open 9).

In addition, it has been reported that $\Delta^9$-THC acts as a partial agonist of CB1R and CBR2 and induces immune and anti-inflammatory effects through CB2R (Pertwee, R. (2008). The diverse CB1 and CB2 receptor pharmacology of three plant cannabinoids: $\Delta^9$-tetrahydrocannabinol, cannabidiol and $\Delta^9$-tetrahydrocannabivarin. British journal of pharmacology 153, 199-215).

The U.S. Food and Drug Administration (FDA) approved $\Delta^9$-THC in 1985 for amelioration of chemotherapy-induced nausea and vomiting, and in 2018 for treatment of Dravet syndrome, pediatric epilepsy, and Lennox-Gastaut syndrome.

It has been reported that CBD can control immune activation not only in human immunodeficiency virus (HIV) but also in Ebola syndrome when orally administered daily at 10-20 mg/kg/day and 1.7-10 mg/kg/day (Konikoff, F. M. (2017). Low-dose cannabidiol is safe but not effective in the treatment for Crohn's disease, a randomized controlled trial. Digestive diseases and sciences 62, 1615-1620).

In particular, recently, the Therapeutic Goods Administration of the Australian Department of Health has suggested that low-dose CBD can be used for treatment of anxiety and insomnia secondary to post-traumatic stress disorder and administered orally or by inhalation or vaporization at 25-40 mg/day for children 10 years old and 50-75 mg/day for adults. In addition, CBD was administered at 1 mg/kg/day for local and systemic chronic pain management, and CBD has been reported to be safe up to 60 mg per day.

It also has been reported that 100 mg of CBD or a combination of 10.8 mg THC and 10 mg CBD is safe and tolerable in healthy volunteers (Expert Committee on Drug Dependence, W.H.O. (2017). Thirty-ninth Meeting, Geneva).

<Example 5> Verification of Stability of CBD-SARS-CoV-2 $M^{Pro}$ Complex Through Molecular Docking Simulation Molecular docking (MD) simulations were used to further evaluate movement and conformational stability of the CBD-SARS-CoV-2 $M^{Pro}$ complex.

It was possible to identify interactions over time for the complex with the highest binding energy. The resulting trajectories were analyzed to determine ligand binding energies, root mean square deviation (RMSD), and total potential energies during 20 ns MD.

As a result of the analysis, the average binding energies of $\Delta^9$-THC and CBD were 164.73 and 93.10 kcal/mol, respectively. These positive binding energies suggest that CBD strongly bound to SARS-CoV-2 $M^{Pro}$ during the molecular docking (MD) run. The $\Delta^9$-THC-SARS-CoV-2 $M^{Pro}$ and CBD-SARS-CoV-2 $M^{Pro}$ complexes exhibited orbital equilibrium after 1500 and 500 ps, respectively, and robust stability during the 20 ns molecular docking (MD) run. Interestingly, $\Delta^9$-THC and CBD showed no further variation during molecular docking (MD) simulation runs in root mean square deviation (RMSD) from SARS-CoV-2 $M^{Pro}$ (FIGS. 7A-7E).

Figure 8:
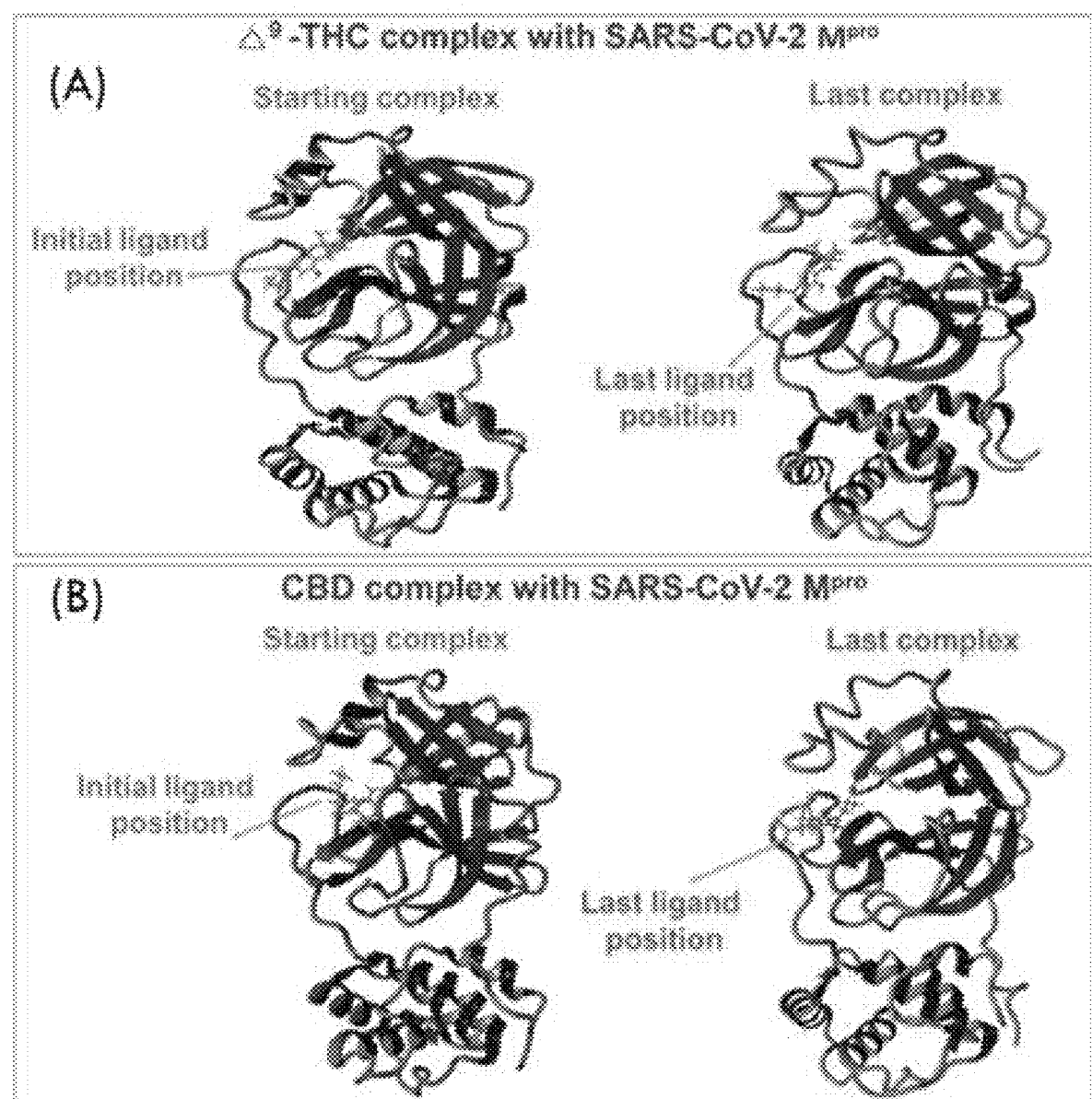
FIG. 8 shows comparison of binding positions of the CBDs-SARS-CoV-2 $M^{Pro}$ complex before and after execution of the molecular docking (MD) simulations for (A) Δ⁹-THC and (B) CBD.

The MD simulation stability profiles of SARS-CoV-2 $M^{Pro}$ using $\Delta^9$-THCA, CBN, and CBDA complexes are shown in FIGS. 7A-7E. Here, CBN showed stability at 1300 ps and $\Delta^9$-THCA showed stability at 1100 ps (FIG. 8). On the other hand, the CBDA molecules exhibited more fluctuations in the root mean square deviation (RMSD) of the backbone and heavy atoms. These observations suggest that the CBDA-SARS-CoV-2 $M^{Pro}$ complex is less stable than the $\Delta^9$-THC-SARS-CoV-2 $M^{Pro}$ and CBD-SARS-CoV-2 $M^{Pro}$ complexes. The potential energies of the $\Delta^9$-THC-SARS-CoV-2 $M^{Pro}$ and CBD-SARS-CoV-2 $M^{Pro}$ complexes exhibited linear trajectories. Therefore, it was determined through the root mean square deviation (RMSD) and binding energies that $\Delta^9$-THC and CBD had binding stability with SARS-CoV-2 $M^{Pro}$ during the 20 ns molecular docking (MD) simulation.

<Example 6> Mechanism of SARS-CoV-2 Inhibition by Cannabinoids (CBDs)

Figure 9A:
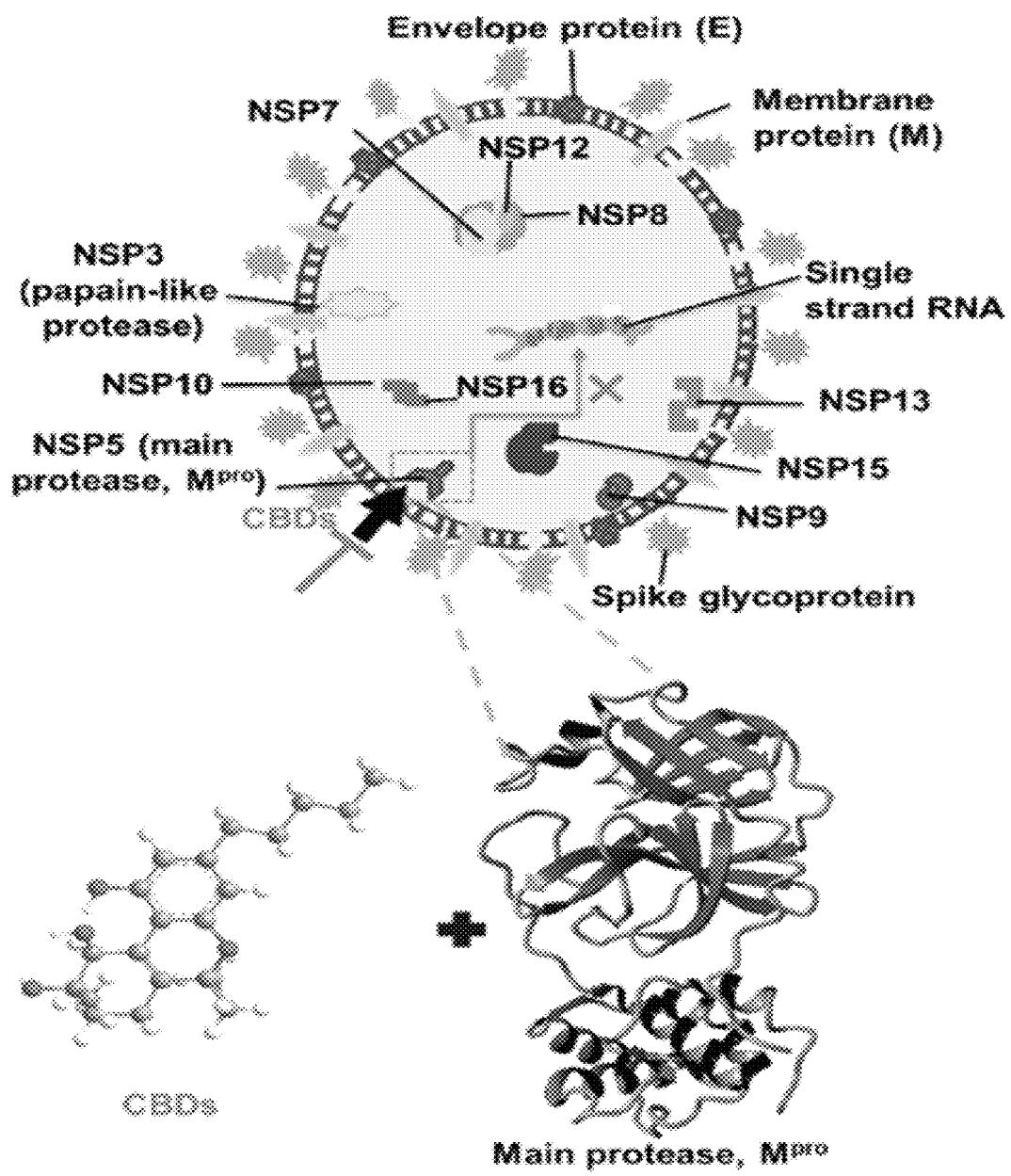
FIG. 9A shows structural features of SARS-CoV-2 and the main SARS-CoV-2 $M^{Pro}$ binding pocket.
Figure 9B:
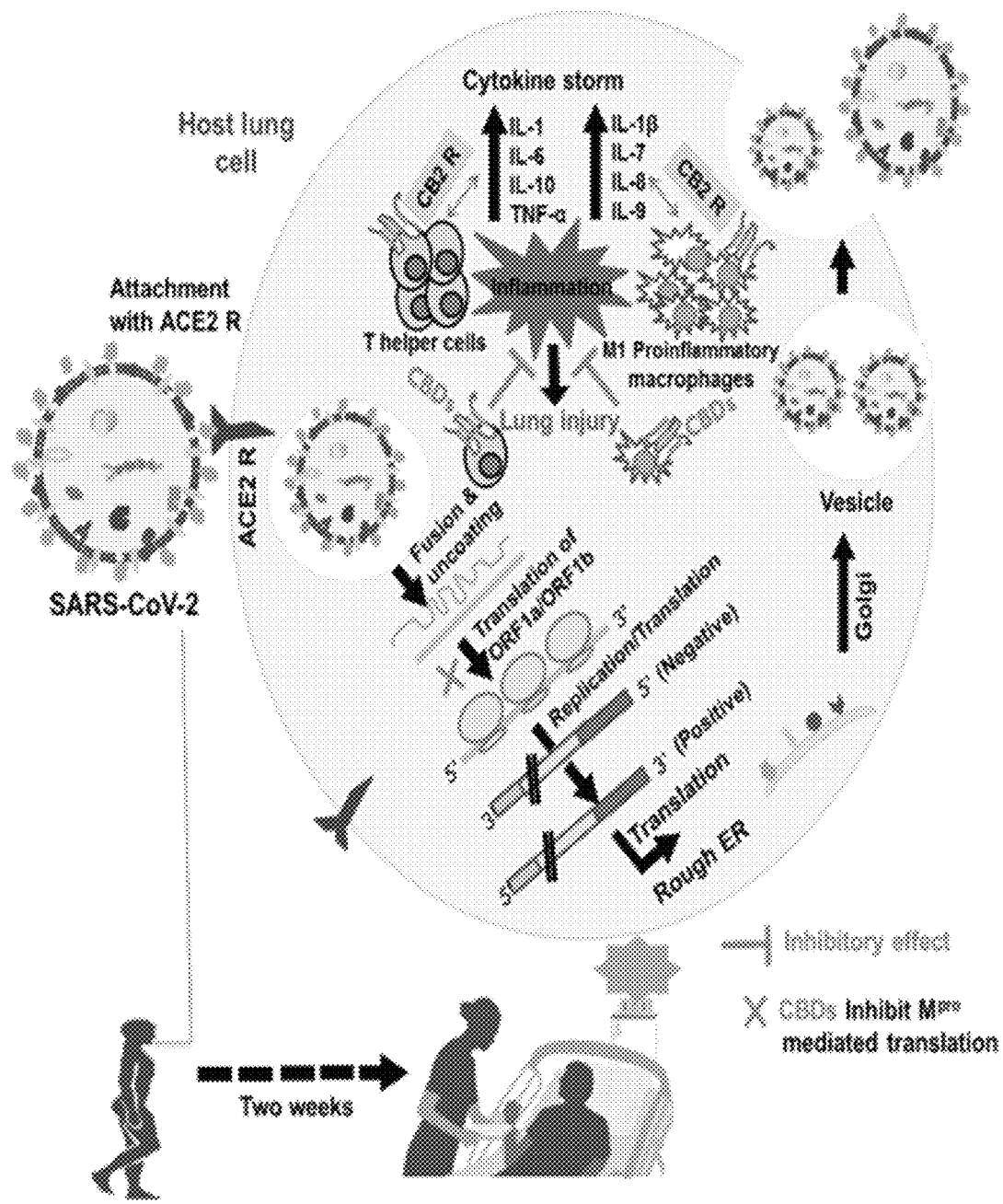
FIG. 9B shows the life cycle of SARS-CoV-2 in the lung cells of the host and a schematic diagram showing that infection of SARS-CoV-2 is initiated by binding between the viral spike glycoprotein and the cell receptor ACE2.

Structural features of SARS-CoV-2 include spike glycoprotein (S-protein, S), chymotrypsin-like main protease, SARS-CoV-2 $M^{Pro}$, papain-like protease, and RNA-dependent RNA polymerase, which play an important role in SARS-CoV-2 development (FIGS. 9A-9B). The life cycle of SARS-CoV-2 in host lung cells is initiated by binding between the spike glycoprotein and the cell receptor ACE2. Spike glycoprotein (S-protein, S) promotes fusion of the virus envelope with the host cell through the endosomal pathway, resulting in cell release of SARS-CoV-2 RNA into the host cell and translation of viral genomic RNA into replicase polyproteins pp1a and 1ab. It is then cut into small pieces by proteolytic enzymes. SARS-CoV-2 $M^{Pro}$ and papain-like proteases are essential for polyprotein processing. Later, subgenomic mRNA is produced by polymerase, and in this pathway, T-helper cells and M1 pro-inflammatory macrophages secrete interleukins that cause inflammation inside the lung cells.

Consequently, inhibition of SARS-CoV-2 $M^{Pro}$ activity blocks viral replication, and importantly, human proteases similar to SARS-CoV-2 $M^{Pro}$ have not been reported yet. Therefore, inhibitors against SARS-CoV-2 $M^{Pro}$ can be considered unlikely to be toxic.

On the other hand, cannabinoids (CBDs) are known to trigger activation of the CB-2 receptors in the lung, induce immunosuppression and apoptosis, increase anti-inflammatory cytokine levels, and inhibit pro-inflammatory cytokine production and induction of regulatory T cells.

According to the results of this study, the molecular docking, DFT, and MD simulations showed that cannabinoids (CBDs) tightly bind with SARS-CoV-2 $M^{Pro}$ and form stable complexes. In particular, the in vitro antiviral activity of CBD and $\Delta^9$-THC of the cannabinoids (CBDs) molecules indicated that SARS-CoV-2 was inhibited in two ways. They bind to SARS-CoV-2 $M^{Pro}$ to inhibit SARS-CoV-2, and bind to cannabinoid receptor-2 (CB-2) and act as an agonist, thereby reducing pro-inflammatory cytokines in the lung cells (FIGS. 9A-9B).

In this study, the present inventors tried to virtual screen cannabinoids (CBDs) with strong binding affinity to SARS-CoV-2 $M^{Pro}$ which is essential for SARS-CoV-2 replication because cannabinoids (CBDs) bind to cannabinoid receptor-2 (CB-2) and inhibit the effects of inflammatory cytokines. As a result of calculation using the density functional theory (DFT) for the 32 cannabinoids (CBDs), $\Delta^9$-THCA and CBD had higher HOMO-LUMO energy gaps than the other molecules, indicating that these molecules could bind stably with SARS-CoV-2 $M^{Pro}$. Also in the molecular docking (MD) simulations, the $\Delta^9$-THC-SARS-CoV-2 $M^{Pro}$ and CBD-SARS-CoV-2 $M^{Pro}$ complexes showed better conformational stability than the $\Delta^9$THCA, CBN and CBDA complexes. In addition, it was confirmed that $\Delta^9$-THC and CBD had excellent in vitro antiviral effects, which supports that $\Delta^9$-THC and CBD are useful lead molecules that can be used alone or in combination with other drugs to treat SARS-CoV-2. Although this study was conducted in silico and in vitro, it is an excellent invention because CBDs can be actively used as a SARS-CoV-2 treatment by elucidating their role in vivo in the future.

What is claimed is:

1. A method for severe acute respiratory syndrome coronavirus 2 (SARS-CoV-2) comprising,
a step of administering to a subject in need thereof an antiviral composition with one or more cannabinoids (CBDs) selected from the group consisting of $\Delta^9$-Tetrahydrocannabinolic acid ($\Delta^9$-THCA) represented by the following Formula 1, $\Delta^9$-Tetrahydrocannabinol ($\Delta^9$-THC) represented by the following Formula 2, Cannabinol (CBN) represented by the following Formula 3, Cannabidiol (CBD) represented by the following Formula 4, and Cannabidiolic acid (CBDA) represented by the following Formula 5,

[Formula 1]

[Formula 2]

[Formula 3]

[Formula 4]

[Formula 5]

2. The method of claim 1,
wherein the cannabinoids are derived from an extract of leaves or unfertilized female flowers of *Cannabis sativa* L. or its fraction.

3. The method of claim 1,
wherein the cannabinoids bind to GLN189, MET165, and GLU166 residues in the SARS-CoV-2 M$^{Pro}$ protease to inhibit protease action.

4. A method of treating severe acute respiratory syndrome coronavirus 2 (SARS-CoV-2) infection comprising,
a step of administering to a subject in need thereof a pharmaceutical composition comprising the antiviral composition according to claim 1 as an active ingredient.

5. The method of claim 4,
wherein the cannabinoids in the antiviral composition act as an agonist of cannabinoid's receptor-2 (CB-2) to inhibit inflammatory cytokines.

6. The method of claim 4,
wherein the antiviral composition is administered at 0.01 to 75 mg/day.

7. A method for promoting severe acute respiratory syndrome coronavirus 2 (SARS-CoV-2) killing comprising,
A step of treating cells with a solution comprising the antiviral composition according to claim 1 as an active ingredient.

8. A method for promoting severe acute respiratory syndrome coronavirus 2 (SARS-CoV-2) killing comprising,
a step of co-administrating the antiviral composition according to claim 1 with one or more drugs selected from the group consisting of lopinavir, chloroquine, and remdesivir.

9. A method of treating severe acute respiratory syndrome coronavirus 2 (SARS-CoV-2) infection comprising,
a step of administering to a subject in need thereof a pharmaceutical composition comprising the antiviral composition according to claim 1 and one or more drugs selected from the group consisting of lopinavir, chloroquine, and remdesivir.

* * * * *